US012336944B2

(12) United States Patent
St. John et al.

(10) Patent No.: US 12,336,944 B2
(45) **Date of Patent: *Jun. 24, 2025**

(54) PATIENT SUPPORT APPARATUS HAVING AN EXTENSION

(71) Applicant: Stryker Corporation, Kalamazoo, MI (US)

(72) Inventors: Connor F St. John, Kalamazoo, MI (US); Christopher Gentile, Sturgis, MI (US); Michael T. Brubaker, Portage, MI (US); Kevin C. Kropp, Gobles, MI (US)

(73) Assignee: Stryker Corporation, Portage, MI (US)

( * ) Notice: Subject to any disclaimer, the term of this patent is extended or adjusted under 35 U.S.C. 154(b) by 198 days.

This patent is subject to a terminal disclaimer.

(21) Appl. No.: 18/080,281

(22) Filed: Dec. 13, 2022

(65) Prior Publication Data

US 2023/0115764 A1 Apr. 13, 2023

Related U.S. Application Data

(60) Continuation of application No. 16/850,579, filed on Apr. 16, 2020, now Pat. No. 11,540,963, which is a (Continued)

(51) Int. Cl.

| | |
|---|---|
| ***A61G 7/05*** | (2006.01) |
| ***A47B 23/00*** | (2006.01) |

(Continued)

(52) U.S. Cl.

CPC ......... *A61G 7/0503* (2013.01); *A61G 7/0506* (2013.01); *A61G 7/053* (2013.01);

(Continued)

(58) Field of Classification Search

CPC .... A61G 7/0503; A61G 7/0506; A61G 7/053; A61G 7/0755; A61G 1/04; A61G 13/10;

(Continued)

(56) References Cited

U.S. PATENT DOCUMENTS

| | | | |
|---|---|---|---|
| 541,339 | A | 6/1895 | Thompson |
| 2,536,366 | A | 1/1951 | George |

(Continued)

FOREIGN PATENT DOCUMENTS

| | | | |
|---|---|---|---|
| AU | 199882929 | A1 | 8/1999 |
| CA | 2301609 | A1 | 3/1999 |

(Continued)

OTHER PUBLICATIONS

English language abstract and machine-assisted English translation for CN 104605635 A extracted from espacenet.com database on Jan. 27, 2022, 5 pages.

(Continued)

*Primary Examiner* — Adam C Ortiz

(74) *Attorney, Agent, or Firm* — Howard & Howard Attorneys PLLC

(57) ABSTRACT

A patient support apparatus having a support structure with a primary support surface for a patient, and an extension manually movable by a user relative to the support structure from a stowed position to an extended position so that the extension provides auxiliary support for the patient in the extended position. A locking device is operable to releasably hold the extension relative to the support structure in the stowed position and the extended position. A release mechanism is operable to manipulate the locking device to release the extension for movement relative to the support structure, and is movable with the extension from the stowed position to the extended position.

16 Claims, 25 Drawing Sheets

Related U.S. Application Data division of application No. 15/261,237, filed on Sep. 9, 2016, now Pat. No. 10,660,809.

(60) Provisional application No. 62/217,588, filed on Sep. 11, 2015.

(51) Int. Cl.

| | |
|---|---|
| ***A61G 1/04*** | (2006.01) |
| ***A61G 5/10*** | (2006.01) |
| ***A61G 7/053*** | (2006.01) |
| ***A61G 7/075*** | (2006.01) |
| ***A61G 13/10*** | (2006.01) |
| ***A61M 5/14*** | (2006.01) |
| ***A61N 1/39*** | (2006.01) |

(52) U.S. Cl.

CPC ......... *A61G 7/0755* (2013.01); *A61M 5/1415* (2013.01); *A61N 1/3968* (2013.01); *A47B 23/00* (2013.01); *A61G 1/04* (2013.01); *A61G 5/1094* (2016.11); *A61G 13/10* (2013.01)

(58) Field of Classification Search

CPC . A61G 5/1094; A61M 5/1415; A61N 1/3968; A47B 23/00

USPC .............................................. 248/56, 49, 65

See application file for complete search history.

(56) References Cited

U.S. PATENT DOCUMENTS

| | | | | |
|---|---|---|---|---|
| 2,551,151 | A | 5/1951 | McMurtrie | |
| 3,054,122 | A | 9/1962 | Sarkus | |
| 3,207,099 | A | 9/1965 | Black | |
| 3,564,627 | A | 2/1971 | Allard | |
| 3,583,760 | A | 6/1971 | McGregor | |
| 3,737,136 | A | 6/1973 | Snurr | |
| 4,672,805 | A | 6/1987 | Moritz | |
| 4,672,898 | A | 6/1987 | Davidson | |
| 4,724,555 | A | 2/1988 | Poehner et al. | |
| 4,803,930 | A | 2/1989 | Crocoli | |
| 5,035,464 | A | 7/1991 | Spallholtz | |
| 5,129,702 | A | 7/1992 | Ervin | |
| 5,425,148 | A | 6/1995 | Ashcraft et al. | |
| 5,745,937 | A | 5/1998 | Weismiller et al. | |
| 5,746,389 | A | 5/1998 | Willmann | |
| 5,802,640 | A | 9/1998 | Ferrand et al. | |
| 6,021,533 | A | 2/2000 | Ellis et al. | |
| 6,071,579 | A | 6/2000 | Green et al. | |
| 6,220,658 | B1 | 4/2001 | Lukawski et al. | |
| 6,295,675 | B1 | 10/2001 | Ellis et al. | |
| 6,357,065 | B1 | 3/2002 | Adams | |
| 6,467,113 | B2 | 10/2002 | Ellis et al. | |
| 6,496,993 | B2 | 12/2002 | Allen et al. | |
| 6,615,744 | B1 | 9/2003 | Eckstein et al. | |
| 6,760,939 | B2 | 7/2004 | Ellis et al. | |
| 6,927,879 | B2 | 8/2005 | Takahashi | |
| 6,930,244 | B1 | 8/2005 | Nebel | |
| 7,028,358 | B2 | 4/2006 | Liu | |
| 7,111,348 | B2 | 9/2006 | Ellis et al. | |
| 7,143,701 | B2 | 12/2006 | Lindstrom et al. | |
| 7,260,860 | B2 | 8/2007 | Chambers et al. | |
| 7,353,556 | B2 | 4/2008 | Ellis et al. | |
| 7,360,260 | B2 | 4/2008 | Gallawa et al. | |
| 7,363,663 | B2 | 4/2008 | Chambers et al. | |
| 7,392,650 | B2 | 7/2008 | Utaki et al. | |
| 7,398,573 | B2 | 7/2008 | Ellis et al. | |
| 7,461,425 | B2 | 12/2008 | Chambers et al. | |
| 7,464,425 | B2 | 12/2008 | Chambers et al. | |
| 7,509,696 | B2 | 3/2009 | Soto et al. | |
| 7,565,710 | B2 | 7/2009 | Chambers et al. | |
| 7,721,657 | B2 | 5/2010 | Carstensen | |
| 7,741,563 | B2 | 6/2010 | Harada et al. | |
| 7,779,493 | B2 | 8/2010 | Lemire et al. | |
| 7,798,072 | B2 | 9/2010 | Becker et al. | |
| 7,832,039 | B2 | 11/2010 | Chambers et al. | |
| 7,845,032 | B2 | 12/2010 | Chambers et al. | |
| 7,895,689 | B2 | 3/2011 | Hayes et al. | |
| 8,069,514 | B2 | 12/2011 | Poulos et al. | |
| 8,104,122 | B2 | 1/2012 | Richards et al. | |
| 8,113,128 | B2 | 2/2012 | Lee | |
| 8,122,546 | B2 | 2/2012 | Chambers et al. | |
| 8,205,564 | B2 | 6/2012 | St. Louis | |
| 8,448,907 | B2 | 5/2013 | Witschen | |
| 8,474,076 | B2 | 7/2013 | Hornbach | |
| 8,474,384 | B2 | 7/2013 | Sundarrao | |
| 8,490,747 | B2 | 7/2013 | Winslow et al. | |
| 8,561,949 | B2 | 10/2013 | Komiya et al. | |
| 8,650,686 | B2 | 2/2014 | Biggie et al. | |
| 8,662,605 | B2 | 3/2014 | McRorie et al. | |
| 8,695,513 | B2 | 4/2014 | Figueras Mitjans | |
| 9,149,400 | B2 | 10/2015 | Serhan | |
| 9,731,829 | B2 | 8/2017 | Gow et al. | |
| 9,867,459 | B2 | 1/2018 | Calderone | |
| 9,988,149 | B2 | 6/2018 | Maillaut | |
| 10,660,809 | B2 | 5/2020 | Graves et al. | |
| 11,540,963 | B2 * | 1/2023 | St. John | A61G 7/053 |
| 2002/0029423 | A1 | 3/2002 | Ellis et al. | |
| 2003/0019042 | A1 | 1/2003 | Ellis et al. | |
| 2004/0261185 | A1 | 12/2004 | Ellis et al. | |
| 2006/0026767 | A1 | 2/2006 | Chambers et al. | |
| 2006/0026768 | A1 | 2/2006 | Chambers et al. | |
| 2006/0220425 | A1 | 10/2006 | Becker et al. | |
| 2006/0282945 | A1 | 12/2006 | Gallawa et al. | |
| 2007/0011817 | A1 | 1/2007 | Ellis et al. | |
| 2007/0017032 | A1 | 1/2007 | Ellis et al. | |
| 2007/0136949 | A1 | 6/2007 | Richards et al. | |
| 2007/0180624 | A1 | 8/2007 | Newkirk et al. | |
| 2007/0227407 | A1 | 10/2007 | Cartensen | |
| 2008/0005847 | A1 | 1/2008 | Chambers et al. | |
| 2008/0005848 | A1 | 1/2008 | Chambers et al. | |
| 2008/0010752 | A1 | 1/2008 | Chambers et al. | |
| 2009/0070942 | A1 | 3/2009 | Chambers et al. | |
| 2009/0249552 | A1 | 10/2009 | Chambers et al. | |
| 2010/0257672 | A1 | 10/2010 | Poulos et al. | |
| 2010/0326331 | A1 | 12/2010 | St. Louis | |
| 2011/0047709 | A1 | 3/2011 | Tarsaud et al. | |
| 2011/0099723 | A1 | 5/2011 | Chambers et al. | |
| 2011/0232001 | A1 | 9/2011 | Poulos et al. | |
| 2012/0023675 | A1 | 2/2012 | Hutchison et al. | |
| 2012/0124746 | A1 | 5/2012 | Andrienko et al. | |
| 2012/0212116 | A1 | 8/2012 | McRorie et al. | |
| 2013/0075130 | A1 | 3/2013 | Kaihotsu et al. | |
| 2014/0026325 | A1 | 1/2014 | Guthrie | |
| 2014/0047641 | A1 | 2/2014 | Thodupunuri et al. | |
| 2014/0215717 | A1 | 8/2014 | Rigsby et al. | |
| 2015/0128347 | A1 | 5/2015 | Hutchison et al. | |
| 2016/0000222 | A1 | 1/2016 | Calderone | |
| 2016/0167555 | A1 | 6/2016 | Allen et al. | |
| 2016/0324702 | A1 | 11/2016 | Smeed | |
| 2017/0071806 | A1 | 3/2017 | Graves et al. | |
| 2020/0237594 | A1 | 7/2020 | St. John et al. | |
| 2020/0237595 | A1 | 7/2020 | Graves et al. | |

FOREIGN PATENT DOCUMENTS

| | | | |
|---|---|---|---|
| CA | 2505097 | A1 | 9/2006 |
| CA | 2505101 | A1 | 9/2006 |
| CN | 104605635 | A | 5/2015 |
| DE | 4216322 | A1 | 11/1993 |
| DE | 69808941 | T2 | 2/2003 |
| DE | 202006004883 | U1 | 6/2006 |
| DE | 202010001100 | U1 | 4/2010 |
| DE | 102010037113 | A1 | 8/2011 |
| EP | 1234565 | A2 | 8/2002 |
| EP | 1011391 | B1 | 10/2002 |
| EP | 1234565 | A3 | 12/2002 |
| EP | 1234565 | B1 | 4/2010 |
| EP | 2698137 | A1 | 2/2014 |
| EP | 2289477 | B1 | 9/2014 |
| EP | 2877058 | A1 | 6/2015 |
| EP | 2954884 | A1 | 12/2015 |
| EP | 3058923 | A1 | 8/2016 |

(56) References Cited

FOREIGN PATENT DOCUMENTS

| | | | |
|---|---|---|---|
| EP | 3058923 | B1 | 4/2018 |
| ES | 1078821 | U | 3/2013 |
| GB | 2313303 | B | 4/2000 |
| JP | 2016028675 | A | 3/2016 |
| KR | 20150059372 | A | 6/2015 |
| TW | 279228 | B | 6/1996 |
| WO | 9909865 | A1 | 3/1999 |
| WO | 9941537 | A1 | 8/1999 |
| WO | 2004021952 | A2 | 3/2004 |
| WO | 2004060257 | A2 | 7/2004 |
| WO | 2014018758 | A1 | 1/2014 |
| WO | 2014201379 | A2 | 12/2014 |
| WO | 2014201379 | A3 | 2/2015 |

OTHER PUBLICATIONS

English language abstract and machine-assisted English translation for DE 10 2010 037 113 A1 extracted from espacenet.com database on Jan. 5, 2022, 9 pages.
English language abstract and machine-assisted English translation for DE 20 2006 004 883 U1 extracted from espacenet.com database on Jan. 5, 2022, 7 pages.
English language abstract and machine-assisted English translation for DE 4216322 A1 extracted from espacenet.com database on Jan. 5, 2022, 12 pages.
English language abstract and machine-assisted English translation for ES 1078821 U extracted from espacenet.com database on Jan. 5, 2022, 5 pages.
English language abstract and machine-assisted English translation for KR 20150059372 A extracted from espacenet.com database on Jan. 27, 2022, 14 pages.
English language abstract for DE 698 08 941 extracted from espacenet.com database on Aug. 23, 2018, 2 pages.
English language abstract for JP 2016-028675 extracted from espacenet.com database on Aug. 23, 2018, 2 pages.
English language abstract for TWI 279228 extracted from espacenet.com database on Aug. 23, 2018, 1 page.
English language abstract not found. However, please see machine assisted English translation for DE 202010001100 extracted for espacenet.com database on Jan. 5, 2017, 11 pages.
Hill-Rom, VersaCare TC Bed Brochure, Mar. 19, 2008, 8 pages, Hill-Rom Services, Inc.
Linet, "Eleganza 3—Bed for Acute Care Brochure", Oct. 2013, 16 pages.
Linet, "Photographs of Linet Hospital Bed", available at least as of Sep. 2016, 5 pages.

* cited by examiner 70
60
110
124
134
130
112
132
116
118
78
82
80
114
84
88
92
76
104
105
142
140
90
100
97
32
96
98
108
103
79
99
94
102
35
34
106
107

108
70
34
35
102
103
98
104
106
107
105
32
92
84
100
100
92
84
97
97
96
96
99
110
110
118
150
150
124
76
124
112
134
142
140
130
134
142
140
130
112
132
116
132
118
116
90
90
78
88
88
80
114
114
80
94
82
82

34
70
35
108
102
103
98
104
106
105
107
32
76
92
100
100
92
84
97
97
84
96
96
99
150
150
76
110
110
118
90
124
142
124
112
134
142
112
130
134
140
130
116
140
132
132
90
116
118
88
88
78
80
114
114
94
80
82
82

70
34
35
92
100
100
92
97
97
96
96
99
32
88
150
150
88
76
110
90
90
110
118
118
120
120
122
122
124
124
112
142
142
112
134
134
130
130
140
140
114
114
94
116
116
132
132
86
86
78
84
84
78
80
80
82
82

70
108
34
35
92
88
76
106
107
102
103
98
104
105
90
84
110
118
120
124
112
130
116
132
122
100
142
140
134
99
114
96
32
150
94
78
80
82

32
96
97
104
98
100
105
79
99
102
100
103
108
106
96
34
35
107

216
226
225
218
224
206
222
228
220
228
212
230
204
209
210
36
232
212
230
200
208
202
210

318
316
320
328
322
326
325
324
304
312
330
310
308
300
302
36

428
416
420
424
422
423
429
423
418
405
407
404
428
412
408
410
400
430
402
36

702
150
96
712
706
718
710
704
716
708
700
705
703

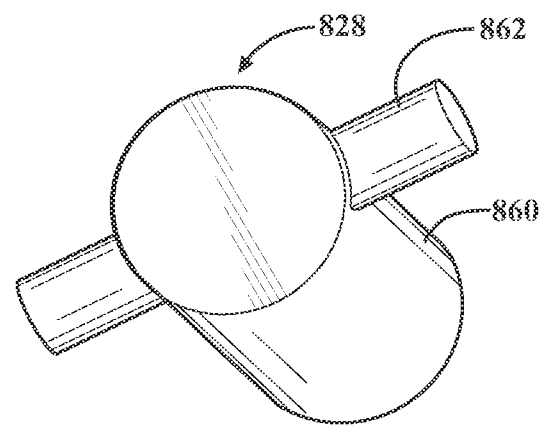
FIG. 21
FIG. 22
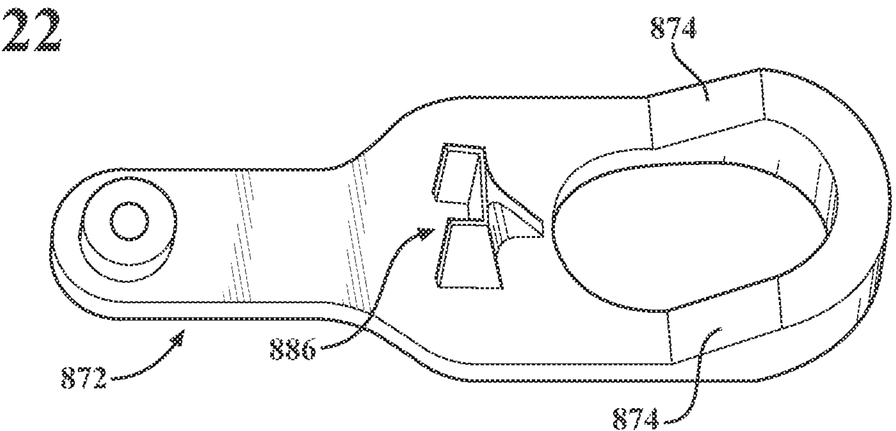
FIG. 23
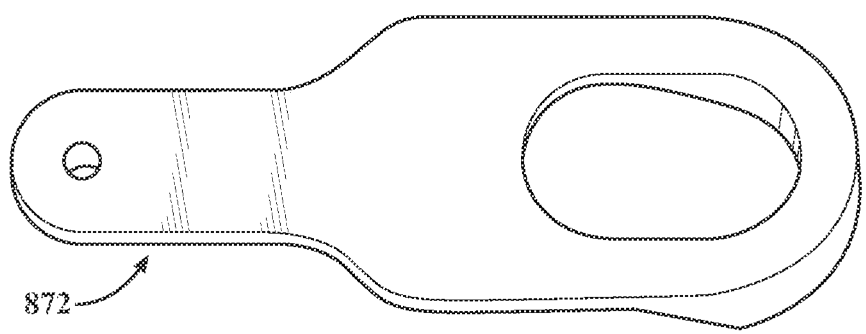

900
922
922
902
920
906
918
916
904
914
60
910
802
916
918
908
925
925
912
922
920
38
902
806

FIG. 26B
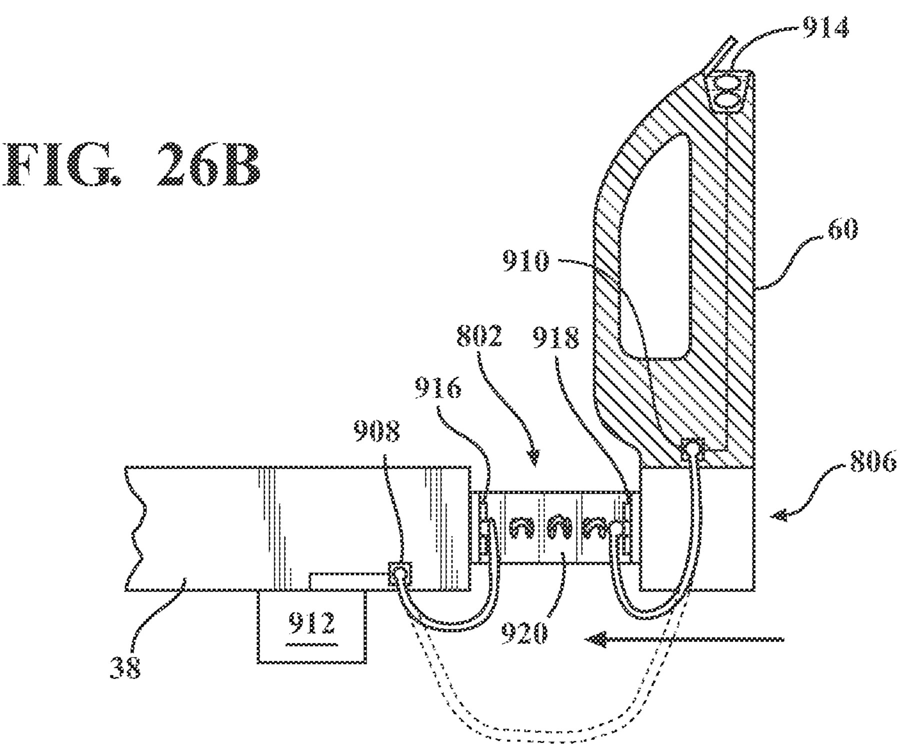
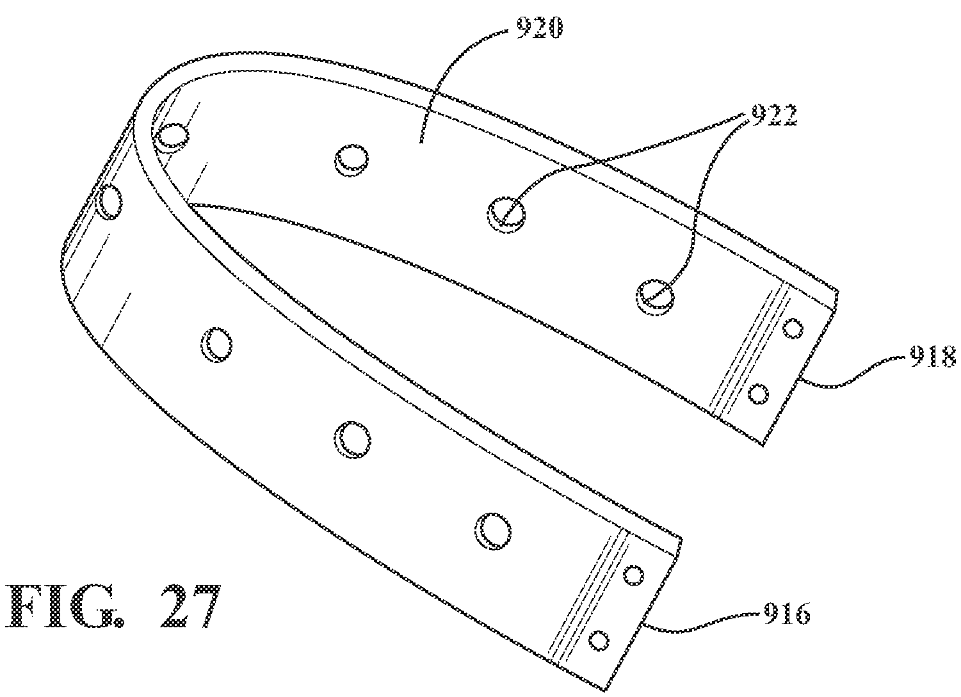
FIG. 27

PATIENT SUPPORT APPARATUS HAVING AN EXTENSION

CROSS-REFERENCE TO RELATED APPLICATIONS

This application is a Continuation of U.S. patent application Ser. No. 16/850,579 filed on Apr. 16, 2020, which is a Divisional of U.S. patent application Ser. No. 15/261,237 filed on Sep. 9, 2016 and issued as U.S. Pat. No. 10,660,809 on May 26, 2020, which claims priority to and the benefit of U.S. Provisional Patent Application No. 62/217,588 filed on Sep. 11, 2015, the disclosures of each of which are hereby incorporated by reference in their entirety.

BACKGROUND

Accessories are often used in conjunction with patient support apparatuses in hospitals and other medical care facilities. Such accessories can include defibrillator trays, bed extensions for accommodating taller patients, food trays, IV poles, operator handles for facilitating transport, egress handles for assisting patients out of bed, foley bag holders, calf supports, foot supports, etc. In some cases, these accessories are manually movable between stowed positions with respect to the patient support apparatus and use positions. In the stowed position, the accessory is stored for later use. In the use position, the accessory is ready to be used by the patient or caregiver.

Telescoping mechanisms are sometimes employed to extend an accessory from the stowed position into the use position. Typical telescoping mechanisms comprise a locking device that locks a telescoping member in an extended position relative to a base support. A separate release device is actuated by the patient or caregiver to unlock the locking device and release the telescoping member so that the telescoping member can be collapsed in order to move the accessory back to the stowed position. In order to actuate the release device, the patient or caregiver normally holds the accessory or the telescoping member with one hand, while engaging the release device with the other hand.

BRIEF DESCRIPTION OF THE DRAWINGS

FIG. 21 is a perspective view of a locking element.

FIG. 22 is a top perspective view of a release member.

FIG. 23 is a bottom perspective view of the release member.

FIG. 25 is a perspective view of a cable support and a cable weaved through openings in the cable support.

FIGS. 26A and 26B are elevational views showing the extension in extended and stowed positions, respectively, with the cable support supporting the cable between the extended and stowed positions.

FIG. 27 is top perspective view of the cable support in a flexed state.

DETAILED DESCRIPTION

Figure 1A:
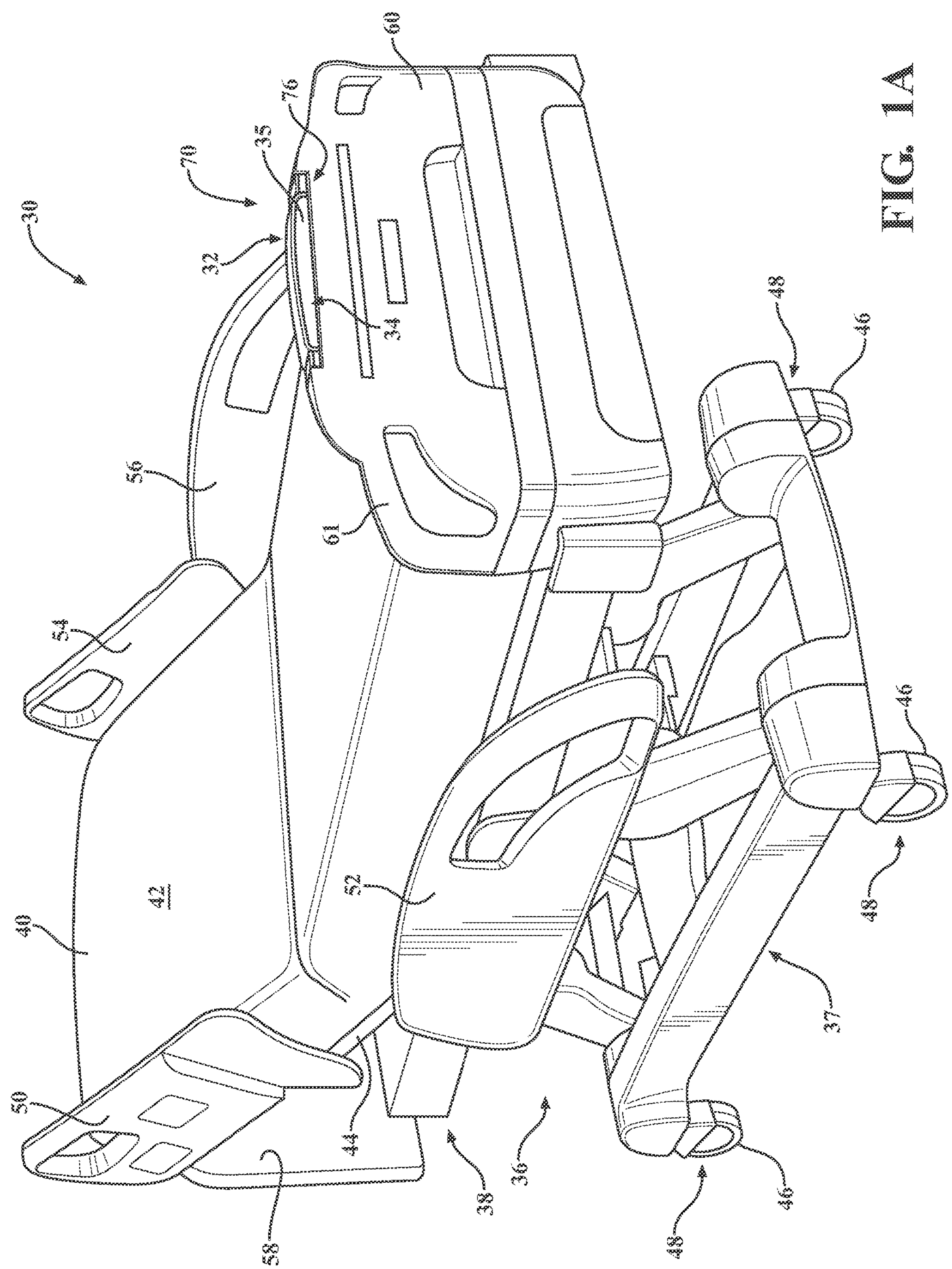
FIG. 1A is a perspective view of a patient support apparatus with a telescoping assembly.
Figure 1B:
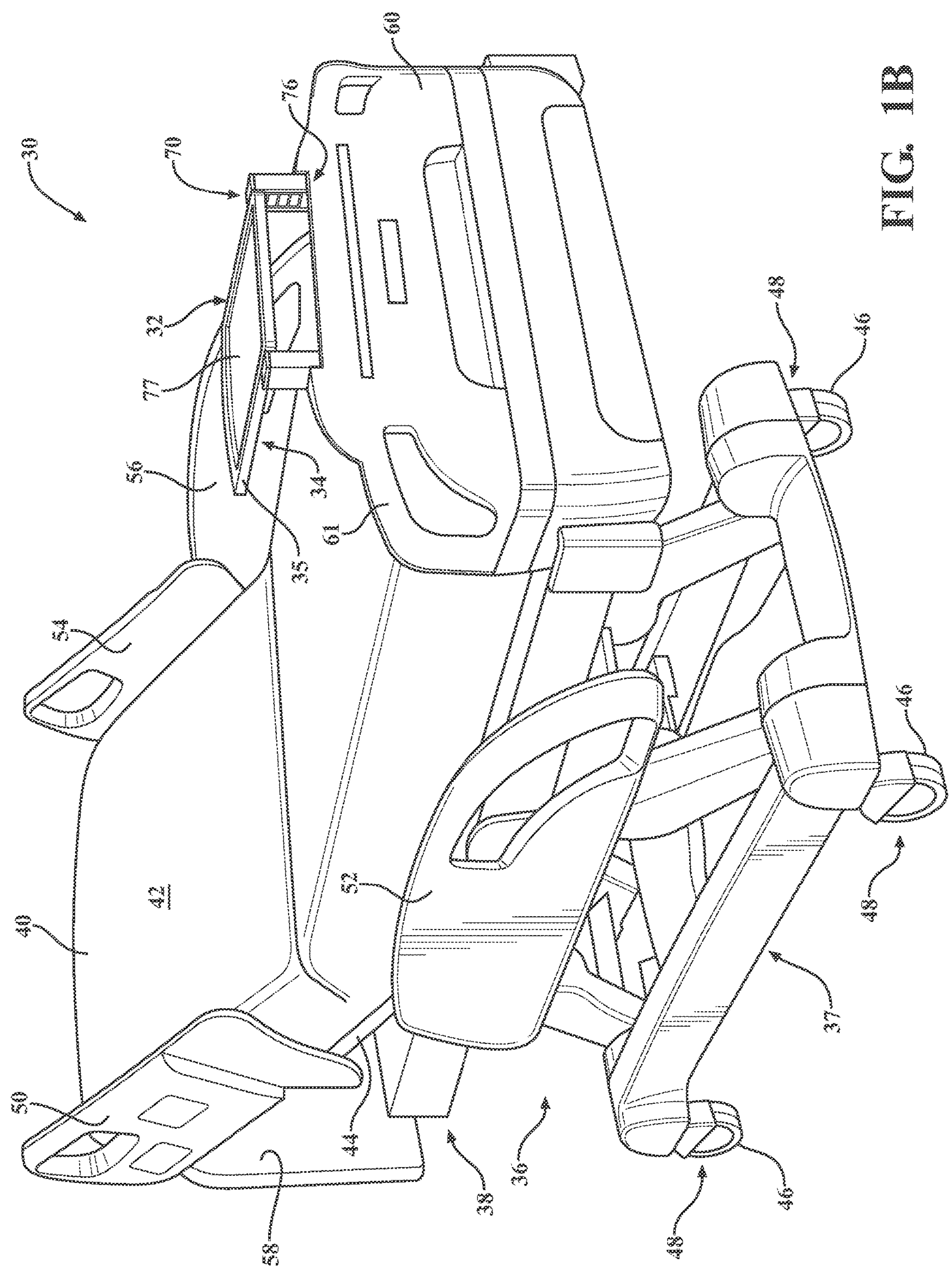
FIG. 1B is a perspective view of the patient support apparatus with an accessory of the telescoping assembly in the use position.

Referring to FIGS. 1A and 1B, a patient support apparatus 30 is shown for supporting a patient. The patient support apparatus 30 illustrated in FIGS. 1A and 1B is a hospital bed. In other embodiments, however, the patient support apparatus 30 may be a stretcher, cot, wheelchair, operating table, or similar apparatus.

A variety of accessories are used on the patient support apparatus 30. Some of the accessories are movable between stowed positions, in which they are stored prior to use, and use positions in which they are ready to be used by a caregiver, patient, or other user. One such accessory 32 for use on the patient support apparatus 30 is shown in FIGS. 1A and 1B. The accessory 32 shown in FIGS. 1A and 1B comprises an accessory member 34 in the form of a defibrillator tray 35. The defibrillator tray 35 is shown in the stowed position in FIG. 1A. In FIG. 1B, the defibrillator tray 35 has been raised from the stowed position by the user and rotated down into the use position. In further embodiments, some of which are described below, other accessories may comprise a hook for an IV pole, an operator handle for facilitating transport, an egress handle for assisting patients, a calf support, a foot support, a bed extension for accommodating taller patients, a food tray, a foley bag holder, or any other movable accessory member.

A support structure 36 provides support for the patient. In some embodiments, one or more of the accessories, such as the accessory 32, may be mounted to the support structure 36. The support structure 36 comprises a base frame 37 and an intermediate frame 38. The intermediate frame 38 is spaced above the base frame 37. A mattress 40 is disposed on the intermediate frame 38. The mattress 40 comprises a patient support surface 42 upon which the patient is supported. The support structure 36 also comprises a patient support deck 44 disposed on the intermediate frame 38. The patient support deck 44 comprises sections to support the mattress 40 and the patient, some of which are pivotable relative to the intermediate frame 38, such as a head section, a seat section, a thigh section, and a foot section. The construction of support structure 36 may take on any known or conventional design.

Four wheels 46 are coupled to the support structure 36 to facilitate transport over floor surfaces. The wheels 46 rotate and swivel relative to the support structure 36 during transport. In the embodiment shown, each of the wheels 46 forms part of a caster 48 coupled to the base frame 37. It should be understood that various configurations of the wheels 46 are contemplated and that each of the four wheels 46 may be non-steerable, steerable, non-powered, powered, or combinations thereof. Fewer or additional wheels are also contemplated. For example, the support structure 36 may comprise four non-powered wheels, along with one or more powered wheels.

Side rails 50, 52, 54, 56 are coupled to the intermediate frame 38. In some embodiments, one or more of the accessories, such as the accessory 32, may be mounted to the side rails 50, 52, 54, 56. The first side rail 50 is positioned at a right head end of the intermediate frame 38. The second side rail 52 is positioned at a right foot end of the intermediate frame 38. The third side rail 54 is positioned at a left head end of the intermediate frame 38. The fourth side rail 56 is positioned at a left foot end of the intermediate frame 38. If the patient support apparatus 30 is a stretcher or a cot, there may be fewer side rails. The side rails 50, 52, 54, 56 are movable between a raised position in which they block ingress and egress into and out of the patient support apparatus 30, and a lowered position in which they are not an obstacle to such ingress and egress.

A headboard 58 and a footboard 60 are coupled to the intermediate frame 38. Operator interfaces 61, such as handles, are shown integrated into the footboard 60 to facilitate movement of the patient support apparatus 30 over the floor surfaces. Separate operator interfaces may be integrated into the headboard 58, the side rails 50, 52, 54, 56, and/or other components of the patient support apparatus 30.

The accessory 32 shown in FIGS. 1A and 1B is arranged to be stowed in the footboard 60. More specifically, the accessory 32 forms part of a telescoping assembly 70 integrated into the footboard 60. In other embodiments, the telescoping assembly 70 is integrated into other components of the patient support apparatus 30, such as the support structure 36, the side rails 50, 52, 54, 56, or other components. In further embodiments, the telescoping assembly 70 is a stand alone assembly that can be used in conjunction with the patient support apparatus 30, but forms no part of the patient support apparatus 30.

The telescoping assembly 70 comprises a telescoping support 76 slidable between a collapsed position and an extended position with respect to the footboard 60. The telescoping support 76 helps to support the accessory member 34 in the use position. The telescoping support 76 is shown in the collapsed position in FIG. 1A, e.g., collapsed into the footboard 60, and in the extended position in FIG. 1B, e.g., extended above the footboard 60. In the embodiment shown, the telescoping support 76 extends vertically with respect to the footboard 60. However, in other embodiments, the telescoping support 76 may be arranged to extend horizontally, or in other directions.

When the user manually moves the accessory 32 from the stowed position to the use position, the accessory 32 carries the telescoping support 76 with it from the collapsed position to the extended position. For example, in FIG. 1B, the defibrillator tray 35 has been moved from the stowed position to the use position by the user, thereby raising the telescoping support 76 into the extended position where the telescoping support 76 has been locked in place. With the telescoping support 76 held in the extended position, the defibrillator tray 35 is supported above the footboard 60 in the rotated-down use position as shown in FIG. 1B.

Figure 2:
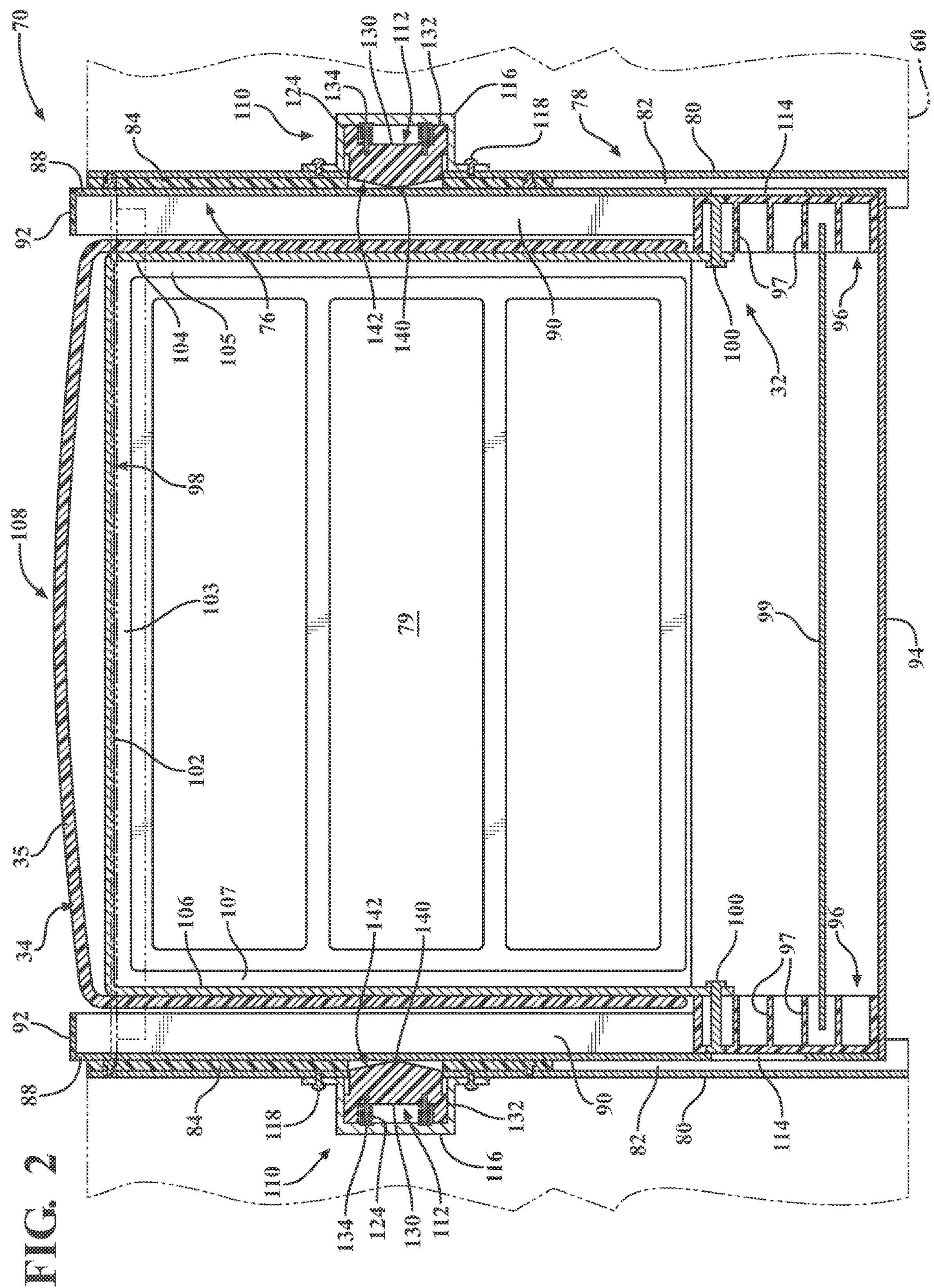
FIG. 2 is a cross-sectional view of the telescoping assembly with the accessory in the stowed position.

Referring to FIG. 2, the telescoping assembly 70 comprises a base support 78 to support the telescoping support 76. The base support 78 comprises a pair of elongate, outer frame members 80. The outer frame members 80 are spaced apart and arranged generally parallel to one another. The outer frame members 80 are U-shaped in cross-section to define a pair of outer channels 82 having open ends. The outer frame members 80 are fixed to the footboard 60. In other embodiments, the outer frame members 80 may be mounted to other components of the patient support apparatus 30. When the outer frame members 80 are formed of metal and the footboard 60 is formed of plastic, then the outer frame members 80 may be integrated into the footboard 60 and fixed thereto by insert molding. The outer frame members 80 may be fastened to the footboard 60 in other ways, such as with fasteners or adhesive. The outer frame members 80 could also be press fit into the footboard 60. In some embodiments, the base support 78 is comprised of the structure of the footboard 60 without the separate outer frame members 80.

Elongate bearing members 84 are mounted and fixed to the outer frame members 80 by fasteners. The bearing members 84 may be fastened to the outer frame members 80 in other ways, such as with adhesive. The bearing members 84 are U-shaped in cross-section and sized to fit in the pair of outer channels 82 with little to no clearance between the bearing members 84 and the outer frame members 80. The bearing members 84 comprise a pair of bearing channels 86 (see FIG. 5) in which the telescoping support 76 slides between the collapsed and extended positions relative to the base support 78.

The bearing members 84 provide bearing surfaces against which the telescoping support 76 slides during operation. The bearing members 84 may be formed of polytetrafluoroethylene (PTFE) known for its low coefficient of friction relative to other polymeric materials. This low friction material helps to prevent binding of the telescoping support 76 during sliding. Other suitable materials for allowing sliding of the telescoping support 76 relative to the base support 78 are also contemplated. It is also contemplated that in some embodiments the bearing members 84 are removed such that the telescoping support 76 slides directly within the base support 78.

The telescoping support 76 comprises a pair of elongate, inner frame members 88 that are sized to slide in the bearing channels 86 as the telescoping support 76 moves between the collapsed and extended positions. The inner frame members 88 are spaced apart and arranged generally parallel to one another. The inner frame members 88 are U-shaped in cross-section to define a pair of inner channels 90. In other embodiments, the telescoping support 76 comprises a single frame member or other structure suitable to be extended for supporting the accessory 32 in the use position.

Upper stops 92 are fixed to the inner frame members 88 at an upper end of the inner frame members 88. In the embodiment shown, the upper stops 92 are in the form of plate-shaped caps welded, or otherwise fixed in some manner, to the inner frame members 88. A lower stop 94 is fixed to the inner frame members 88 at an opposing end. The lower stop 94 is shown as a elongate, flat bar that spans between the inner frame members 88 to add structural support to the telescoping support 76 and to hold the inner frame members 88 in their parallel and spaced relationship. The lower stop 94 may be welded or otherwise affixed to the inner frame members 88 at lower ends of the inner frame members 88.

Figure 7:
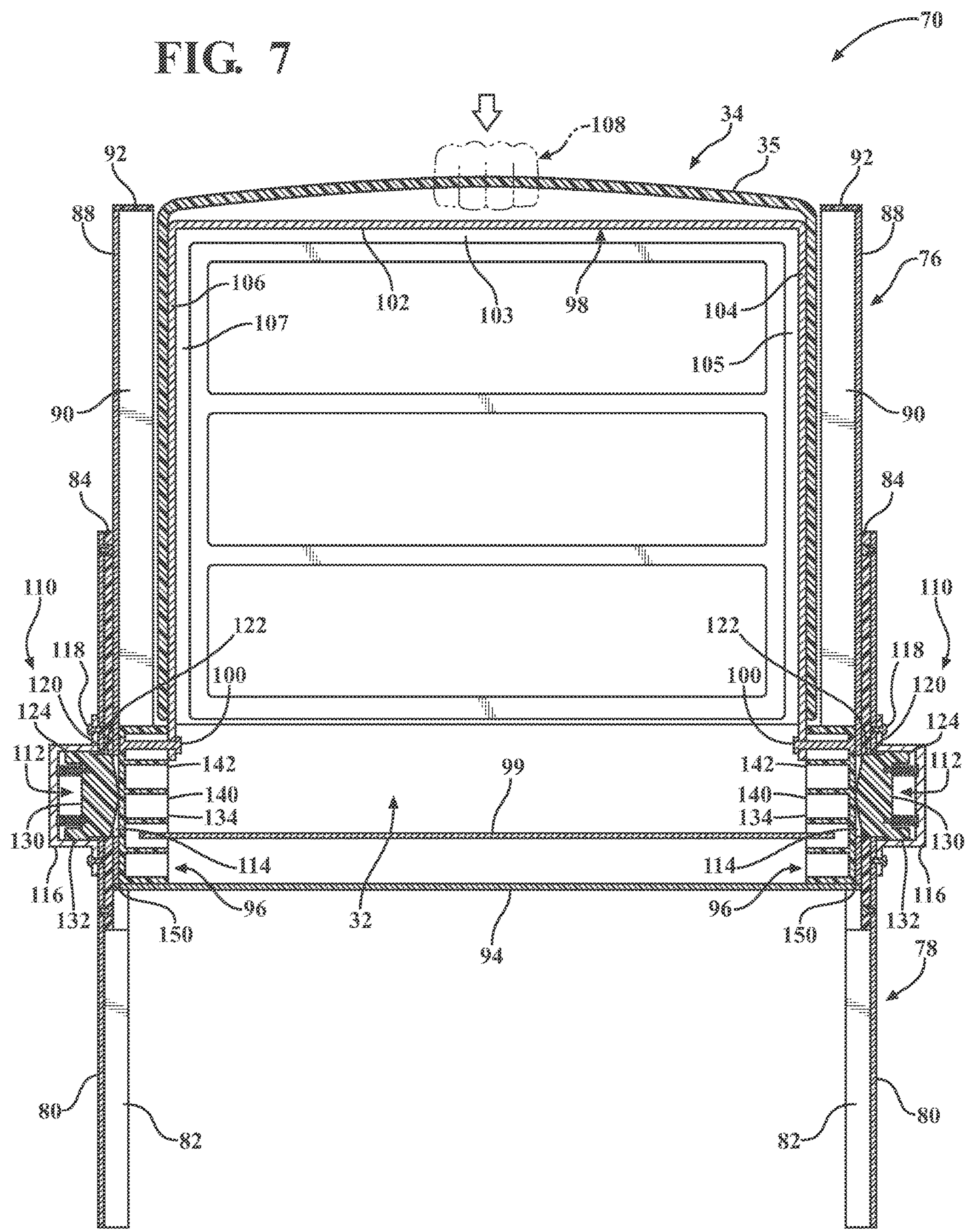
FIG. 7 is a cross-sectional view of the telescoping assembly with the accessory beginning to lower the telescoping support to a collapsed position.

The stops 92, 94 act to capture slide members 96 of the accessory 32 in the inner channels 90. Capturing the slide members 96 of the accessory 32 in the inner channels 90 effectively couples movement of the slide members 96 to the telescoping support 76 so that the telescoping support 76 can be moved indirectly by the user thereby making direct contact with the telescoping support 76 unnecessary. For instance, referring briefly to FIG. 3, when the user is raising the accessory 32 to place the accessory 32 in the use position, the slide members 96 of the accessory 32 engage the upper stops 92 so that any further raising of the accessory 32 raises the inner frame members 88. Likewise, when the user is lowering the accessory 32 back to the stowed position as shown in FIG. 7, the slide members 96 engage the lower stop 94 to also push the inner frame members 88 back to the collapsed position, if needed, i.e., in the event the inner frame members 88 are unable to lower under the force of gravity, such as when the inner frame members 88 are arranged horizontally.

The slide members 96 slide in the inner channels 90 when the accessory 32 moves between the stowed position and the use position. The slide members 96 shown in FIG. 2 have internal ribs 97 for added structural support. In other embodiments, the slide members 96 are solid. The slide members 96 are formed of plastic or other material. A support member 99 is fixed to and interconnects the slide members 96. The support member 99 extends between the slide members 96 so that the slide members 96 are maintained at a fixed distance from one another to facilitate uniform sliding of the slide members 96 in the inner channels 90. The support member 99 shown in FIG. 2 is a flat metal support bar, but other shapes and materials are contemplated.

Figure 8A:
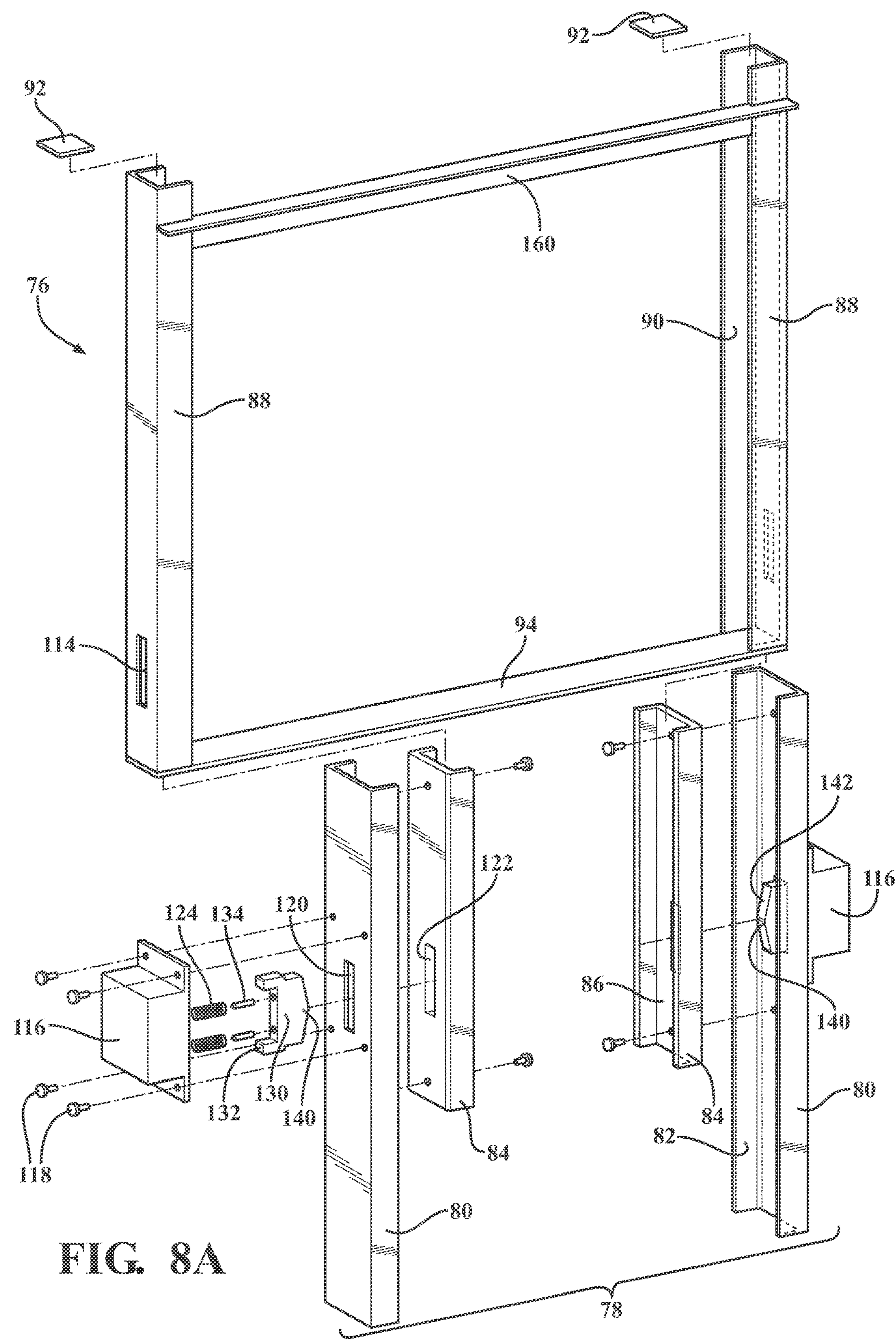
FIGS. 8A and 8B collectively are an exploded view of the telescoping assembly.
Figure 8B:
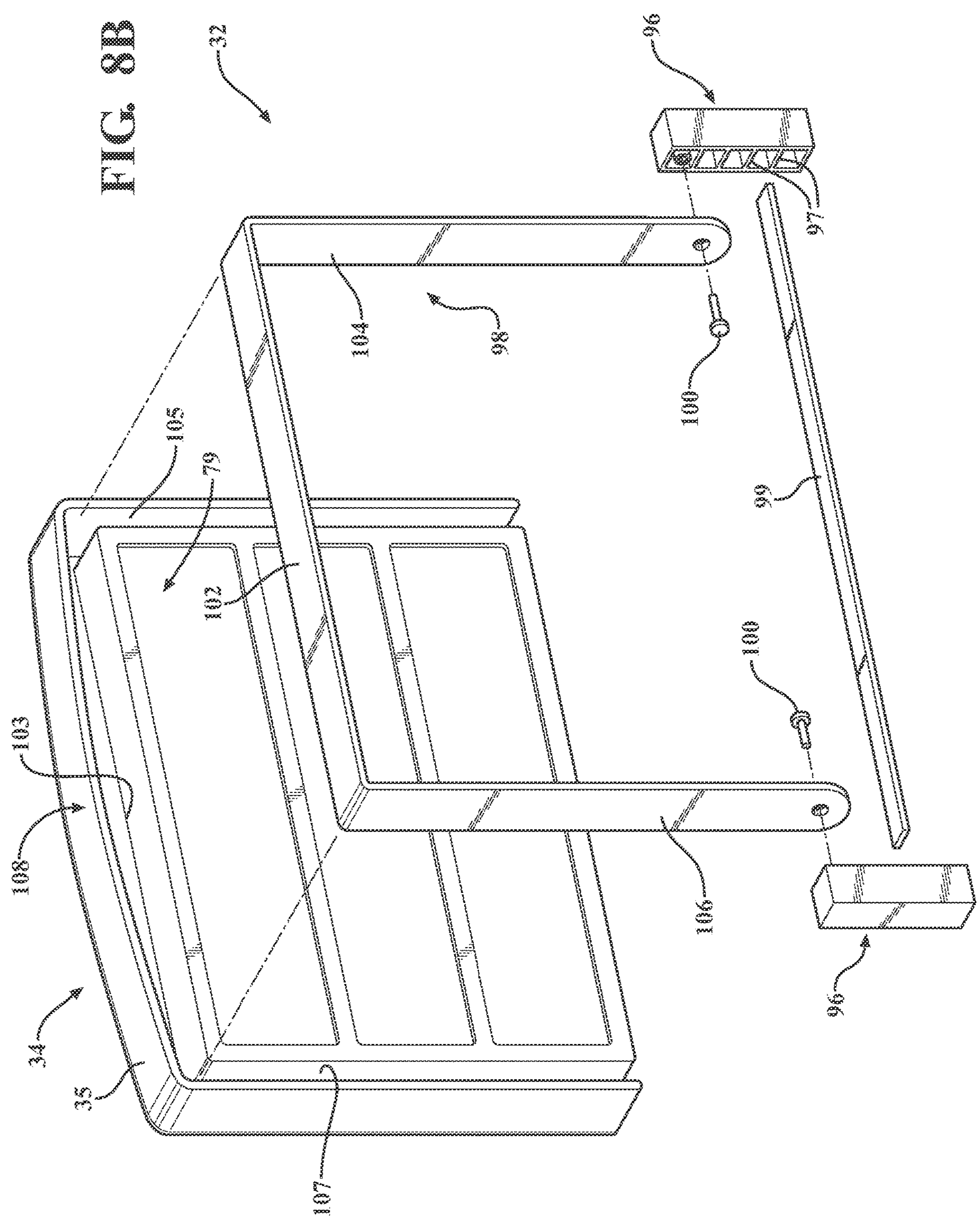

The accessory 32 comprises an accessory frame 98 pivotally connected to the slide members 96 by pivot pins 100 (see also exploded view in FIG. 8B). The accessory frame 98 may be formed of metal to provide structural support to the accessory member 34. The accessory frame 98 has three segments 102, 104, 106 making the accessory frame 98 three-sided. The accessory member 34 has a top surface 77 (see FIG. 1B) and a bottom surface 79. The bottom surface 79 comprises three grooves 103, 105, 107 for receiving the three segments 102, 104, 106 of the accessory frame 98 so that the accessory frame 98 is substantially concealed from view when the accessory member 34 is in the use position.

When the accessory member 34 is formed of plastic, the accessory frame 98 may be insert molded in the accessory member 34. The accessory frame 98 may also be fastened to the accessory member 34 by fasteners, adhesive, welding, or other suitable methods. The accessory member 34 is pivotally coupled to the slide members 96 by the pivot pins 100 so that the user is able to rotate the accessory member 34 into the use position in which the accessory member 34 is arranged generally perpendicular to the telescoping support 76, as shown in FIG. 1B.

Figure 3:
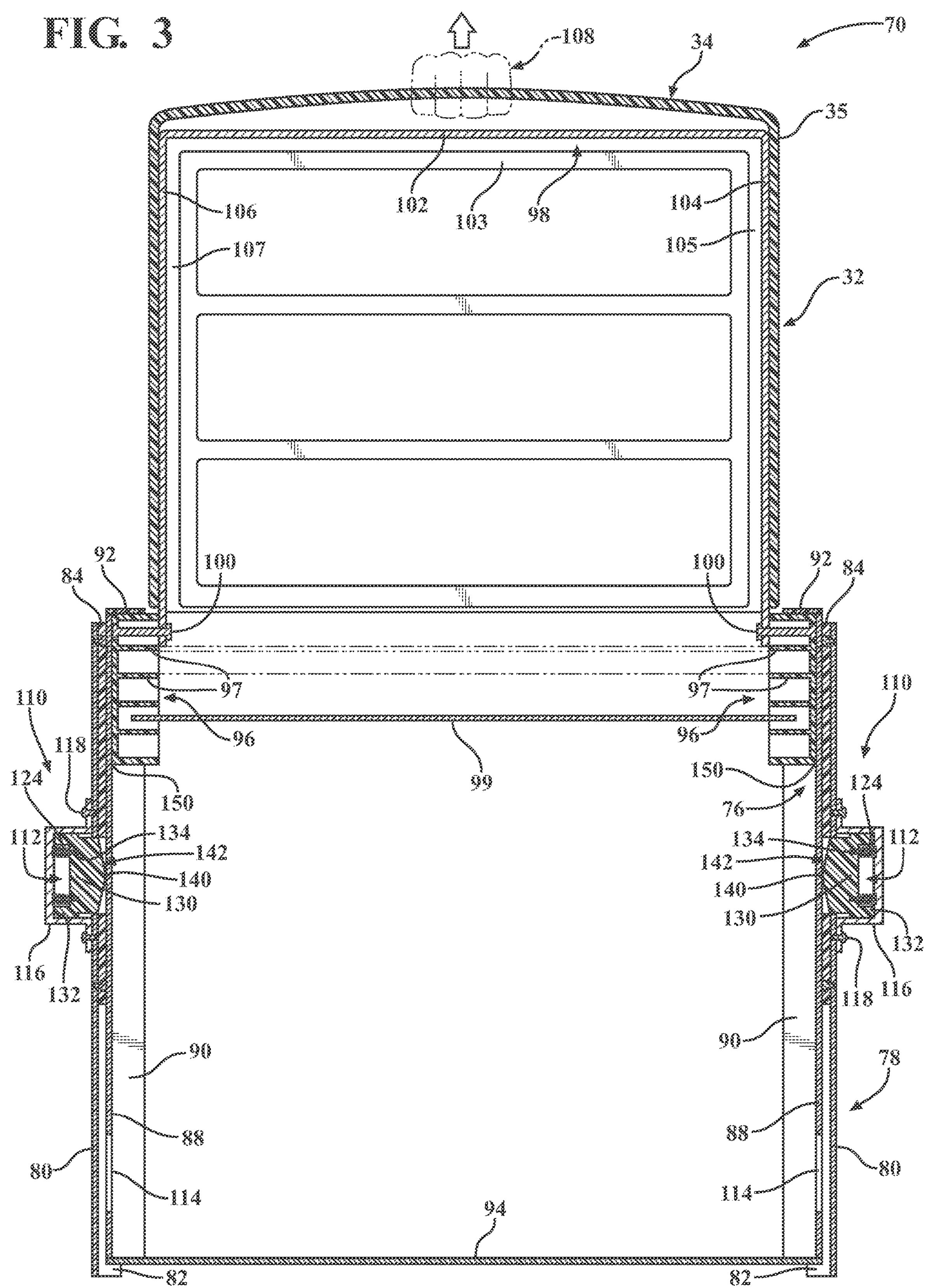
FIG. 3 is a cross-sectional view of the telescoping assembly with the accessory raised with respect to a telescoping support.
Figure 4:
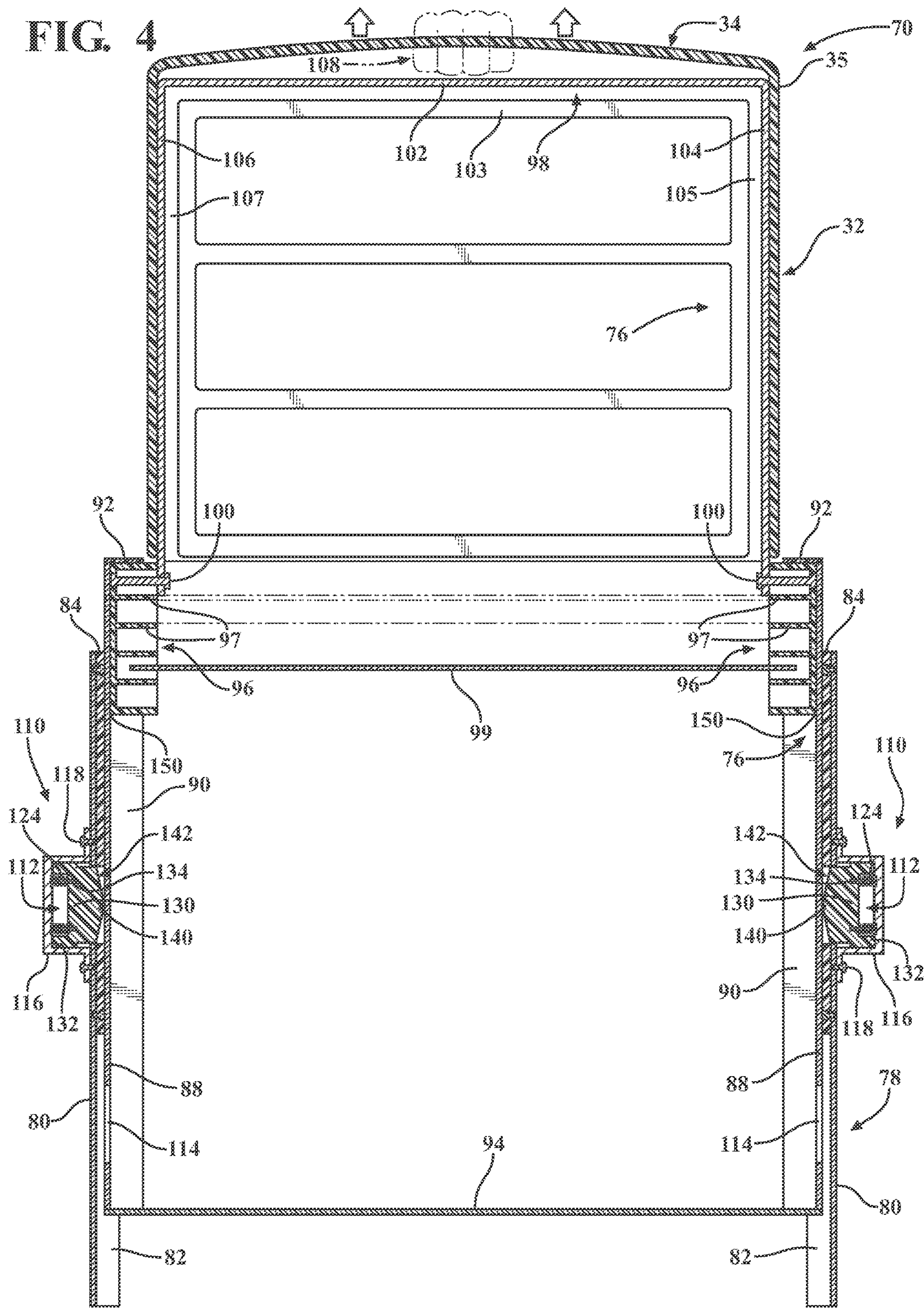
FIG. 4 is a cross-sectional view of the telescoping assembly with the accessory beginning to raise the telescoping support with respect to a base support.

As shown in FIGS. 3 and 4, the accessory 32 has a user interface 108 to enable the user to manually move the accessory 32 between the stowed and use positions. In the embodiment shown, the user interface 108 is a front wall of the accessory member 34. The user grasps the user interface 108 to apply a force to the accessory member 34 to raise the accessory member 34 from the stowed position to the use position. The user interface 108 may comprise a separate handle fixed to the accessory member 34 or simply any surface of the accessory member 34 that the user would logically engage to move the accessory member 34 between the stowed and use positions.

Figure 5:
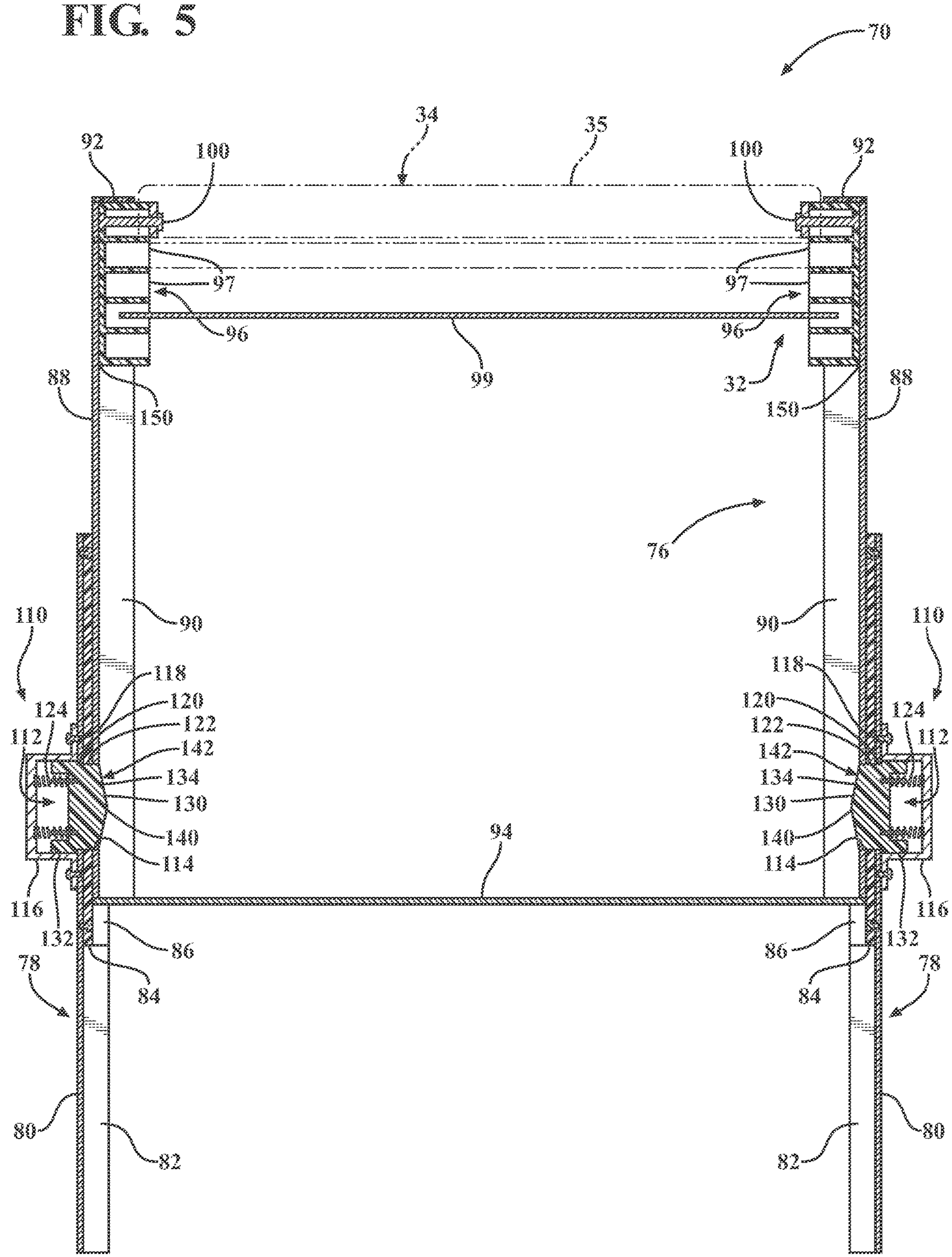
FIG. 5 is a cross-sectional view of the telescoping assembly with the accessory in the use position and the telescoping support in an extended position.

Referring to FIG. 5, locking devices 110 are operable to releasably engage and hold the telescoping support 76 in the extended position. Each locking device 110 comprises a latch 112. The telescoping support 76 comprises a pair of corresponding catches 114 (see also FIG. 4) for receiving the latches 112 to hold the telescoping support 76 in the extended position. The catches 114 shown are openings in the inner frame members 88. Each of the catches 114 are dimensioned so that the latches 112 are able to protrude into the catches 114 to hold the telescoping support 76 in the extended position. The latches 112 are shown disposed in the catches 114 in FIG. 5. Although two locking devices 110 are shown for engaging and holding the telescoping support 76 in the extended position, more or fewer locking devices 110 may also be utilized. For instance, in some embodiments, only a single locking device 110 is used.

Housings 116 protect and support the latches 112 for sliding movement. The housings 116 are mounted to the outer frame members 80 by fasteners 118 thereby coupling the latches 112 to the base support 78. In this configuration, the latches 112 slide transverse relative to the base support 78 between locked and unlocked positions. Both the outer frame members 80 and the bearing members 84 comprise openings 120, 122 (see FIG. 8A) through which the latches 112 can freely move to engage the catches 114.

Biasing devices 124 apply biasing forces to the latches 112 to bias the latches 112 toward the telescoping support 76 so that the latches 112 engages the catches 114 when the telescoping support 76 reaches the extended position, e.g., when the openings in the inner frame members 88 align vertically with the latches 112. Two biasing devices 124 are positioned between each housing 116 and associated latch 112. In other embodiments, more or fewer biasing devices may be employed. For example, only a single biasing device 124 may be used to bias each latch 112 into the associated catch 114. The biasing devices 124 shown are compression springs. Other types of biasing devices may be used including leaf springs, torsion springs, or other resilient elements.

Each of the latches 112 comprises a main body 130 having upper and lower surfaces and opposing side surfaces extending therebetween. Legs 132 extend rearwardly from the main body 130. The legs 132 are dimensioned to fit inside the respective housing 116 with little clearance thereabout to enable smooth lateral sliding of the latch 112 with respect to the housing 116. Pins 134 are embedded in or otherwise fixed to the main body 130 of the latch 112. The pins 134 project rearwardly from a rear surface of the main body 130 between the legs 132. The biasing devices 124 are disposed about the pins 134 to bias the rear surface of the main body 130 away from the housing 116.

A tip 140 protrudes forward from the main body 130 of each latch 112. The tip 140 has a front profiled surface 142 that extends at obtuse angles from each of the upper and lower surfaces to define a peak of the tip 140. The tips 140 are configured so that, as shown in FIG. 5, the tips 140 protrude into the inner channels 90 in the locked position such that the profiled surface 142 of each tip 140 is exposed in the inner channels 90. At the same time, the upper and lower surfaces of the main body 130 of each latch 112 protrude further into the openings 120, 122 in the outer frame member 80 and the bearing member 84 to reach the associated catch 114. In the locked position, the upper and lower surfaces terminate at an inside surface of the inner frame members 88 so that the upper and lower surfaces are not protruding into the inner channels 90. The profiled surface 142 of each latch 112 is profiled for engagement by one of the slide members 96 when the slide members 96 slide downwardly in the inner channels 90. Other shapes of the profiled surface 142 are contemplated. The profiled surface 142 may extend at an acute angle from one of the upper and lower surfaces of the latch 112. The profiled surface 142 may be arcuate between the upper and lower surfaces. The profiled surface 142 may be semi-spherical. The profiled surface 142 may be any shape capable of being engaged to release the latch 112.

Deactivator portions 150 of the slide members 96 are configured to engage the profiled surfaces 142 of the latches 112 to release the latches 112 when the user moves the accessory 32 from the use position back toward the stowed position. In the embodiment shown, the deactivator portions 150 are lower edges on the slide members 96. In order to disengage the latches 112, the user first grasps the user interface 108 and rotates the accessory member 34, e.g., the defibrillator tray 35, back to its upright position. Next, the user applies a downward force at the user interface 108 (or simply allows gravity to perform the work) to slide the slide members 96 downwardly in the inner channels 90 until the deactivator portions 150, e.g., the edges of the slide members 96, engage the profiled surfaces 142 of the latches 112. Upon applying further downward force, the deactivator portions 150 of the slide members 96, which are held apart the fixed distance by the support member 99, act to push the latches 112 laterally outwardly of the inner channels 90 thereby disengaging each of the latches 112 from the catches 114 against the biasing force of the biasing devices 124, as shown in FIG. 7. Other shapes of the deactivator portions 150 are contemplated. For instance, the deactivator portions 150 may each comprise a ramp shaped to engage the profiled surfaces 142 of the latches 112. The deactivator portions 150 may also be arcuate. The deactivator portions 150 may be any shape capable of engaging the latches 112. The latches 112 and the deactivator portions 150 may employ other shapes configured to interact so that the deactivator portions 150 are able to disengage the latches 112 from the catches 114.

Disengaging each of the latches 112 enables movement of the telescoping support 76 from the extended position back to the collapsed position. With the tips 140 pushed out of the inner channels 90 by the slide members 96, further downward movement of the slide members 96 engages the lower stop 94 and begins downward movement of the telescoping support 76. In the embodiment shown, the tips 140 are pushed out of the inner channels 90 such that the tips 140 no longer protrude into the inner channels 90, but are nevertheless present in the catches 114. Additionally, the upper and lower surfaces of the main body 130 have been pushed out of the catches 114 to reside solely in the openings 120, 122 in the outer frame members 80 and bearing members 84. As a result, when the user applies further downward force at the user interface 108, the slide members 96 further push against the lower stop 94, and concurrently, edges of the inner frame members 88 that define the catches 114 engage the profiled surface 142. This engagement acts to further push the tips 140 of the latches 112 laterally outwardly toward their starting positions shown in FIGS. 2-4.

The deactivator portions 150 are located remotely from the user interface 108. As a result, when the user stows the accessory member 34 using the user interface 108, the deactivator portions 150 deactivate the locking devices 110 remotely from the user thereby enabling movement of the telescoping support 76 from the extended position back to the collapsed position without additional user intervention or manipulation. This is particularly useful in embodiments in which the locking devices 110 are inaccessible by the user. For instance, in the embodiment shown, the locking devices 110 are integrated into the footboard 60 and located in a pocket in the footboard 60. The user is unable to reach the locking devices 110 directly to unlock the locking devices 110. However, with the configuration of the deactivator portions 150 being remote from the user interface 108, the user is able to manipulate the user interface 108 outside of the pocket to slide the deactivator portions 150 into the pocket to reach the locking devices 110 and unlock the locking devices 110.

Transition of the accessory member 34, e.g., the defibrillator tray 35, from the stowed position to the use position, and associated movement of the telescoping support 76 from the collapsed position to the extended position, is illustrated in FIGS. 2-6. FIG. 2 shows the accessory 32 in the stowed position, before the user has grasped onto the accessory member 34 at the user interface 108. Likewise, the telescoping support 76 remains in the collapsed position.

FIG. 3 shows the user's hand grasping onto the accessory member 34 at the user interface 108 and raising the accessory 32 upwardly out of the stowed position until the slide members 96 engage the upper stops 92. The latches 112 remain unlocked since the catches 114 are not yet aligned with the latches 112. Instead, the latches 112 are held outwardly by the inner frame members 88 against the biasing force of the biasing devices 124. The biasing devices 124 are slightly compressed.

FIG. 4 shows further movement of the accessory 32 upwardly away from the stowed position. Since the slide members 96 are abutting the upper stops 92, this further upward movement results in corresponding upward movement of the telescoping support 76. As shown in FIG. 4, the inner frame members 88 of the telescoping support 76 have been raised slightly relative to the outer frame members 80. The latches 112 remain unlocked since the catches 114 are still not aligned with the latches 112. Instead, the latches 112 are held outwardly by the inner frame members 88 against the biasing force of the biasing devices 124. The biasing devices 124 are slightly compressed.

FIG. 5 shows the accessory 32 in the use position. When the accessory 32 is in the use position, the telescoping support 76 is fully raised to the extended position. In this position, the inner frame members 88 of the telescoping support 76 have been raised enough so that the latches 112 align with the catches 114. As a result, since the biasing devices 124 urge the latches 112 into engagement, once this alignment occurs, the latches 112 automatically protrude into the catches 114 to releasably engage and hold the inner frame members 88.

Figure 6:
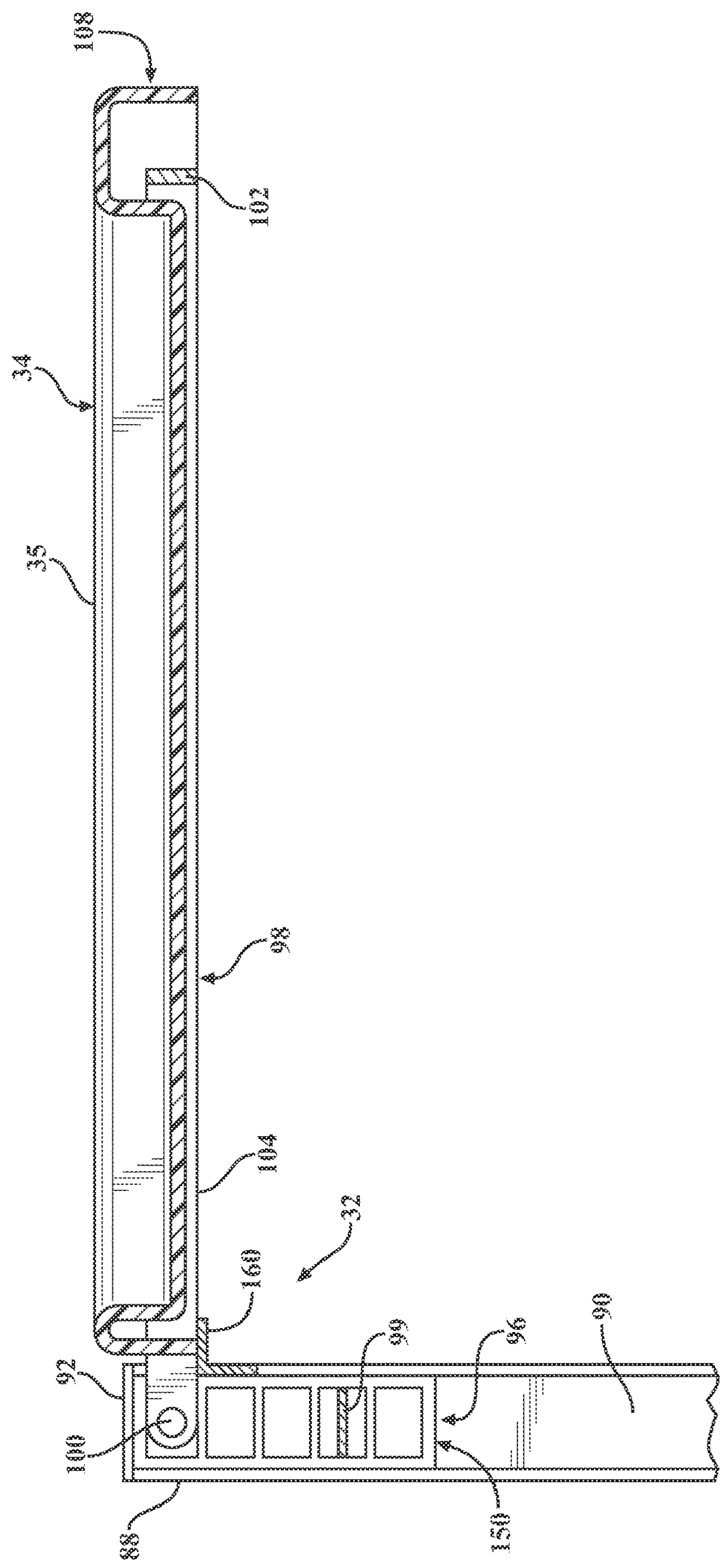
FIG. 6 is a partial cross-sectional view of the accessory in the use position.

Referring to FIGS. 6 and 8A, an angle bracket 160 is fixed to and interconnects the inner frame members 88 to support the accessory member 34 during use. The angle bracket 160 is located and dimensioned so that, when the accessory member 34 is rotated down into the use position, the slide members 96 are likewise abutting the upper stops 92 thereby preventing over rotation of the accessory member 34, e.g., the defibrillator tray 35, relative to the inner frame members 88.

Transition of the accessory 32 from the use position back to the stowed position, and associated movement of the telescoping support 76 from the extended position back to the collapsed position, is basically a reverse of the progression shown in FIGS. 2-6. FIG. 7 shows the additional step of the deactivator portions 150 releasing the latches 112 from the catches 114. With the latches 112 disengaged, the telescoping support 76 can be moved from the extended position to the collapsed position (step not shown). When the user applies further downward force at the user interface 108, the slide members 96 further push against the lower stop 94. Concurrently, edges of the inner frame members 88 that define the catches 114 engage the profiled surfaces 142 to further push the tips 140 of the latches 112 laterally outwardly toward their starting positions depicted in FIGS. 2-4.

Figure 9:
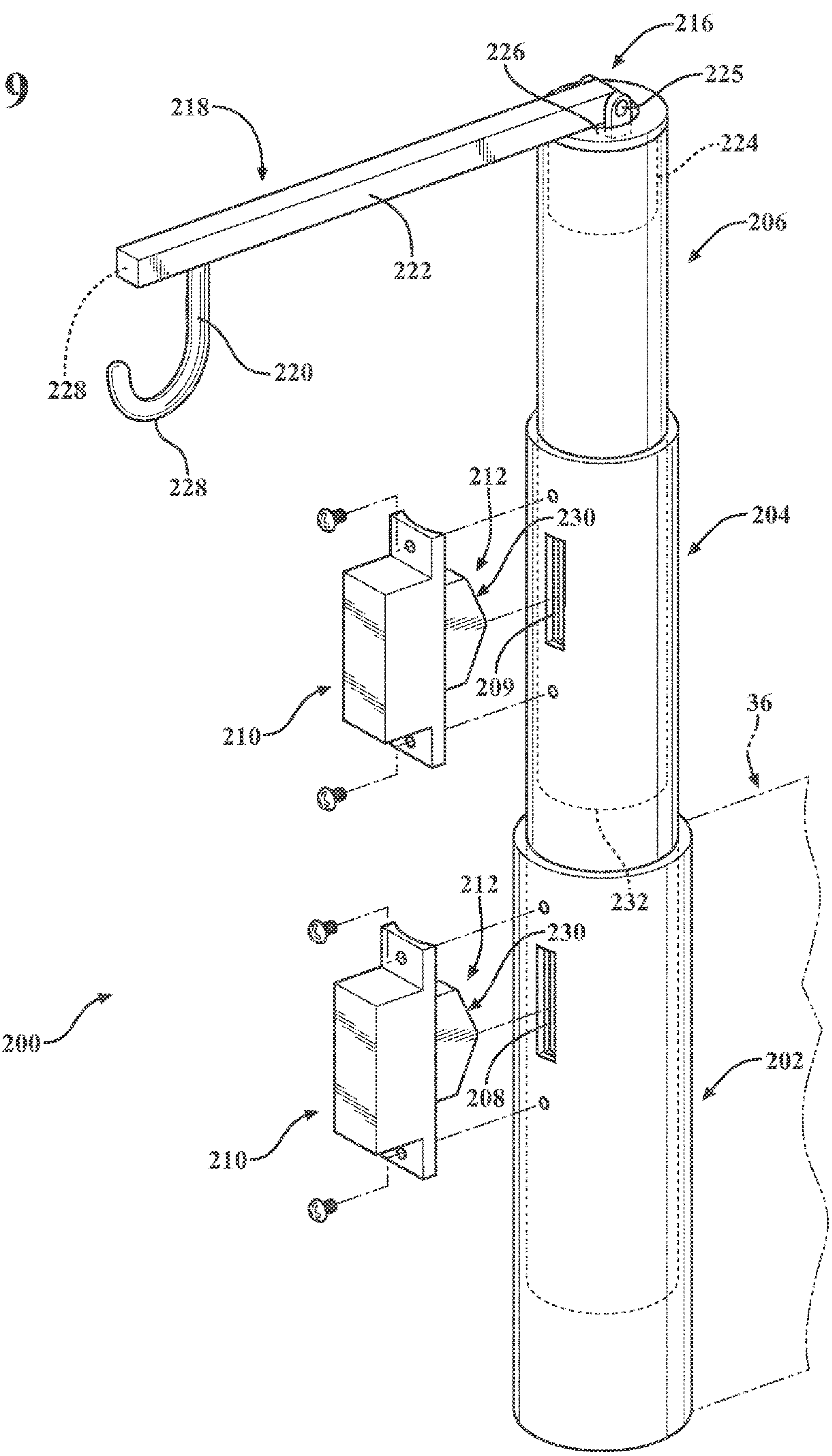
FIG. 9 is a perspective and partially exploded view of an alternative telescoping assembly.
Figure 10:
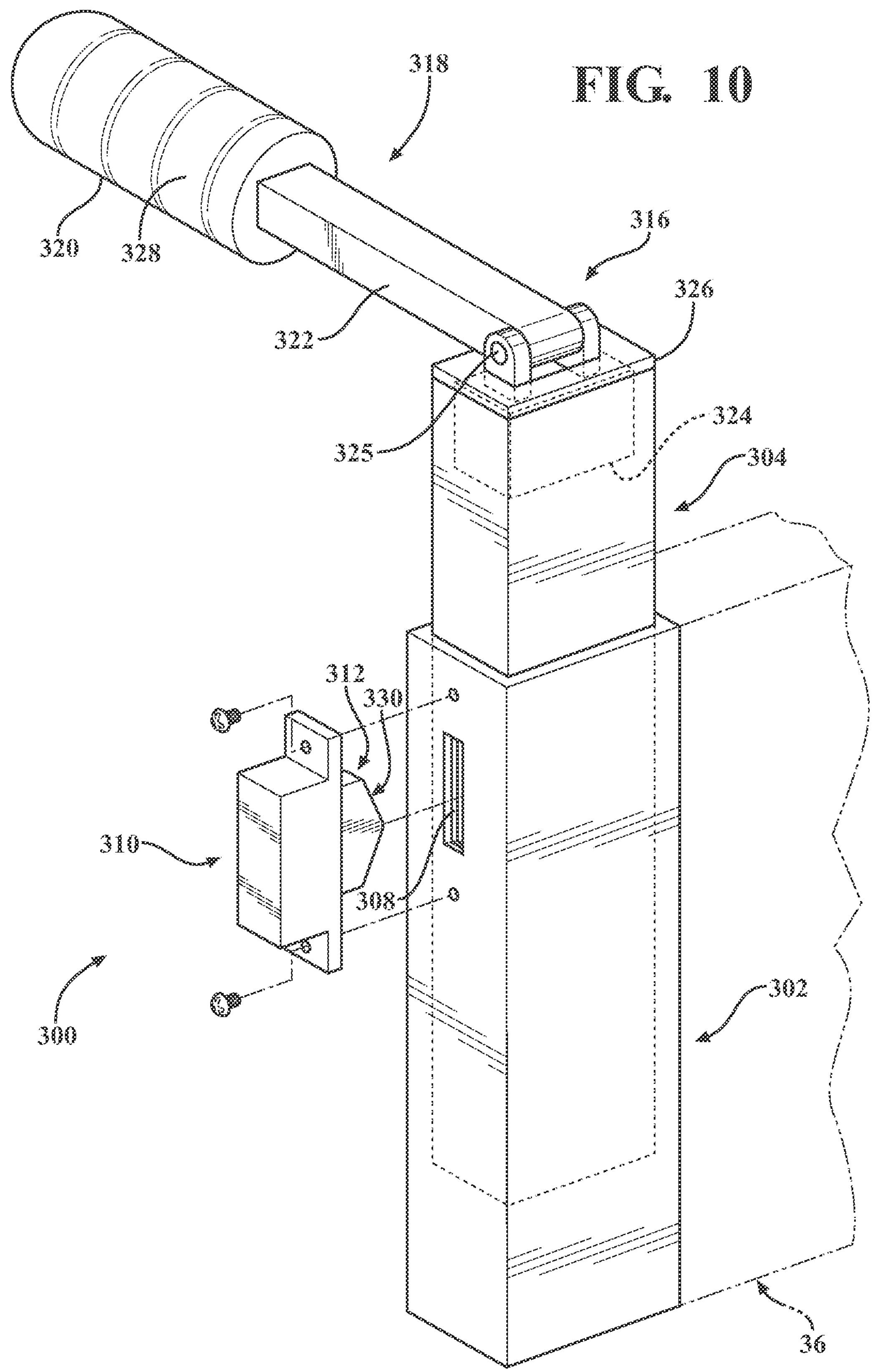
FIG. 10 is a perspective and partially exploded view of another alternative telescoping assembly.
Figure 11:
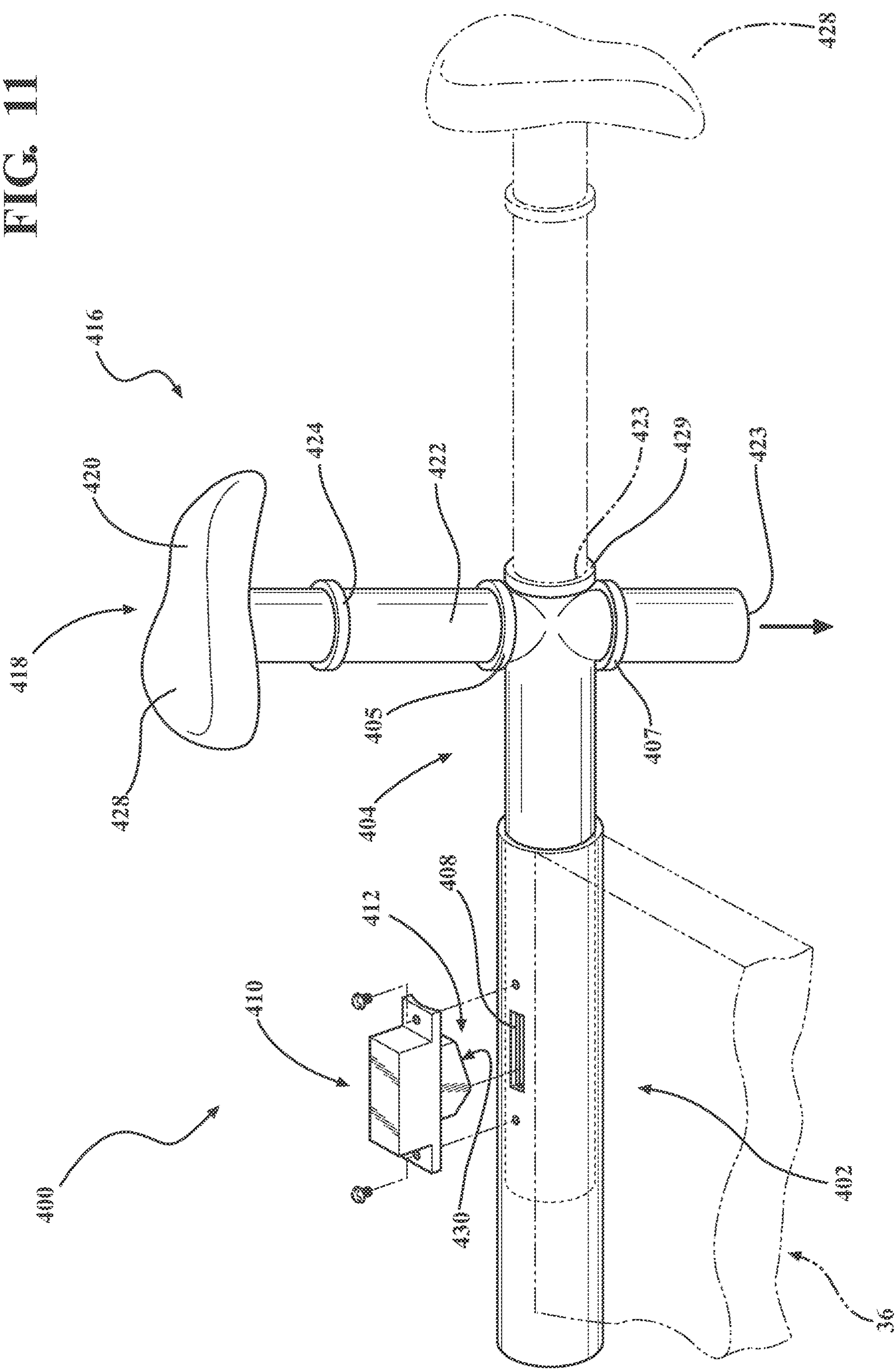
FIG. 11 is a perspective and partially exploded view of another alternative telescoping assembly.

Referring to FIGS. 9-11, alternative telescoping assemblies are shown. In the embodiment of FIG. 9, a telescoping assembly 200 is employed as an IV pole. A base support 202 is fixed to the support structure 36 of the patient support apparatus 30, such as to the base frame 37 or the intermediate frame 38. Two telescoping supports 204, 206 are employed in this embodiment. The telescoping supports 204, 206 are slidable relative to the base support 202 between collapsed positions and extended positions. The base support 202 and telescoping supports 204, 206 are hollow tubes having cylindrical outer walls. In other embodiments, additional telescoping supports may be employed, to provide three, four, or more telescoping supports slidable between collapsed and extended positions.

The telescoping supports 204, 206 comprise catches 208, 209 like the catches described in the prior embodiments. Additionally, locking devices 210 having latches 212 are employed to releasably engage and hold the telescoping supports 204, 206 in the extended positions in the same manner as previously described.

An accessory 216 comprises an accessory member 218. In this embodiment, the accessory member 218 comprises a hook 220 and an extension arm 222 fixed to the hook. The accessory 216 also comprises a slide member 224 pivotally coupled to the extension arm 222 by a pivot pin 225. The slide member 224 is captured in the telescoping support 206 by upper stop 226. Upper stop 226 acts similar to the upper stops 94 of prior described embodiments, but has a center opening defined therein for allowing the extension arm 222 to slide through the upper stop 226 when moving the accessory 216 between the stowed position and the use position. The center opening, however, is sized so that the hook 220 is unable to pass through the center opening.

The accessory 216, shown in the use position in FIG. 9, is stowed in a similar manner as that described with respect to the prior embodiments. In this embodiment, user interface 228 is an outer surface of the hook 220 or the extension arm 222. The user grasps the user interface 228 and rotates the accessory member 218, e.g., both the hook 220 and the extension arm 222, to an upright position. In this position, the user can then apply a downward force on the user interface 228 (or allow gravity to take over) until the slide member 224 engages a profiled surface 230 of the latch 212 holding the telescoping support 206 in the extended position. Once the user applies further downward force, the slide member 224 disengages the latch 212 from the catch 209 in the same manner as described in the prior embodiments. As a result, the telescoping support 206 is released and allowed to move toward its collapsed position.

During subsequent movement of the telescoping support 206, a lower edge 232 of the telescoping support 206 engages the profiled surface 230 of the latch 212 holding the telescoping support 204 in the extended position. Applying further force to the telescoping support 206, by virtue of applying force to the user interface 228 (hook 220 now abuts the upper stop 226), the user is able to disengage the latch 212 holding the telescoping support 204 from the catch 208 in the same manner as the slide member 224 disengaged the other latch 212. With all latches 212 disengaged, the telescoping supports 204, 206 are able to be moved to their collapsed positions and the accessory 216 can be placed in the stowed position.

In the embodiment of FIG. 10, a telescoping assembly 300 is employed as an operator handle assembly or egress handle assembly. A base support 302 is fixed to the support structure 36 of the patient support apparatus 30, such as to the base frame 37 or the intermediate frame 38. A telescoping support 304 is slidable relative to the base support 302 between a collapsed position and an extended position. The base support 302 and telescoping support 304 are hollow tubes having rectangular outer walls.

The telescoping support 304 comprises a catch 308 like the catches described in the prior embodiments. Additionally, a locking device 310 having a latch 312 is employed to releasably engage and hold the telescoping support 304 in the extended position in the same manner as previously described.

In this embodiment, an accessory 316 comprises an accessory member 318. The accessory member 318 comprises a handle 320 and an extension arm 322 fixed to the handle 320. The accessory 316 also comprises a slide member 324 pivotally coupled to the extension arm 322 by a pivot pin 325. The slide member 324 is captured in the telescoping support 304 by upper stop 326. Upper stop 326 acts similar to the upper stop 226 of the embodiment of FIG. 9. The upper stop 326 has a center opening defined therethrough for allowing the extension arm 322 to slide through the upper stop 326 when moving the accessory 316 between the stowed position and the use position. The center opening, however, is sized so that the handle 320 is unable to pass through the center opening.

The accessory 316, shown in the use position in FIG. 10, is stowed in a similar manner as that described with respect to the prior embodiments. In this embodiment, user interface 328 is an outer surface of the handle 320. The user grasps the user interface 328 and rotates the accessory member 318, e.g., both the handle 320 and the extension arm 322, to an upright position. In this position, the user can then apply a downward force on the user interface 328 (or allow gravity to take over) until the slide member 324 engages the profiled surface 330 of the latch 312 holding the telescoping support 304 in the extended position.

Once the user applies further downward force on the handle 320, the slide member 324 disengages the latch 312 from the catch 308 in the same manner as described in the prior embodiments. As a result, the telescoping support 304 is released and allowed to move toward its collapsed position as the accessory 316 is moved to the stowed position. The handle 320 is configured so that the handle 320 abuts the upper stop 326 when fully stowed in the telescoping support 304.

In the embodiment of FIG. 11, a telescoping assembly 400 is employed as a calf support assembly. A base support 402 is fixed to the support structure 36 of the patient support apparatus 30, such as to the base frame 37 or the intermediate frame 38. A telescoping support 404 is slidable relative to the base support 402 between a collapsed position and an extended position. The base support 402 and telescoping support 404 are hollow tubes having cylindrical outer walls.

The telescoping support 404 comprises a catch 408 like the catches described in the prior embodiments. Additionally, a locking device 410 having a latch 412 is employed to releasably engage and hold the telescoping support 404 in the extended position in the same manner as previously described.

In this embodiment, an accessory 416 comprises an accessory member 418. The accessory member 418 comprises a calf support seat 420 attached to an extension shaft 422. The extension shaft 422 is fixed to the calf support seat 420 and extends away from the calf support seat 420. The accessory 416 also comprises a shaft flange 424 fixed about the extension shaft 422 in spaced relation to the calf support seat 420. In this embodiment, the portion of the extension shaft 422 extending below the shaft flange 424 acts as the slide member from prior embodiments.

The telescoping support 404 has upper and lower rims 405, 407 fixed to its cylindrical outer wall. The rims 405, 407, together with associated openings (not shown) in the outer wall, define a transverse cylindrical passage that passes through the telescoping support 404 in a cross-wise manner to a main cylindrical passage. During use, the portion of the extension shaft 422 extending below the shaft flange 424 is inserted into the transverse cylindrical passage until the flange 424 is seated and rests on the upper rim 405. When so inserted, the user grasps the calf support seat 420 and pulls the accessory member 418 from the collapsed position to the extended position (extended position shown in FIG. 11). In this position, the latch 412 engages the catch 408.

The accessory member 418 is stowed in a similar manner as that described with respect to the prior embodiments. In this embodiment, user interface 428 is an outer surface of the calf support seat 420. The user grasps the user interface 428, pulls the extension shaft 422 from the transverse cylindrical passage and then re-inserts the extension shaft 422 into the main cylindrical passage via an end of the telescoping support 404, as shown by the hidden lines in FIG. 11. The user continues to slide the extension shaft 422 into a hollow space defined in the telescoping support 404 until a lower edge 423 of the extension shaft 422 engages the profiled surface 430 of the latch 412 holding the telescoping support 404 in the extended position.

Once the user applies further force on the user interface 428 the lower edge 423 of the extension shaft 422 disengages the latch 412 from the catch 408 in the same manner as described in the prior embodiments. As a result, the telescoping support 404 is released and allowed to move toward its collapsed position as the accessory 416 is moved to the stowed position. The flange 424 engages a top 429 of the telescoping support 404 in the stowed position.

Figure 12:
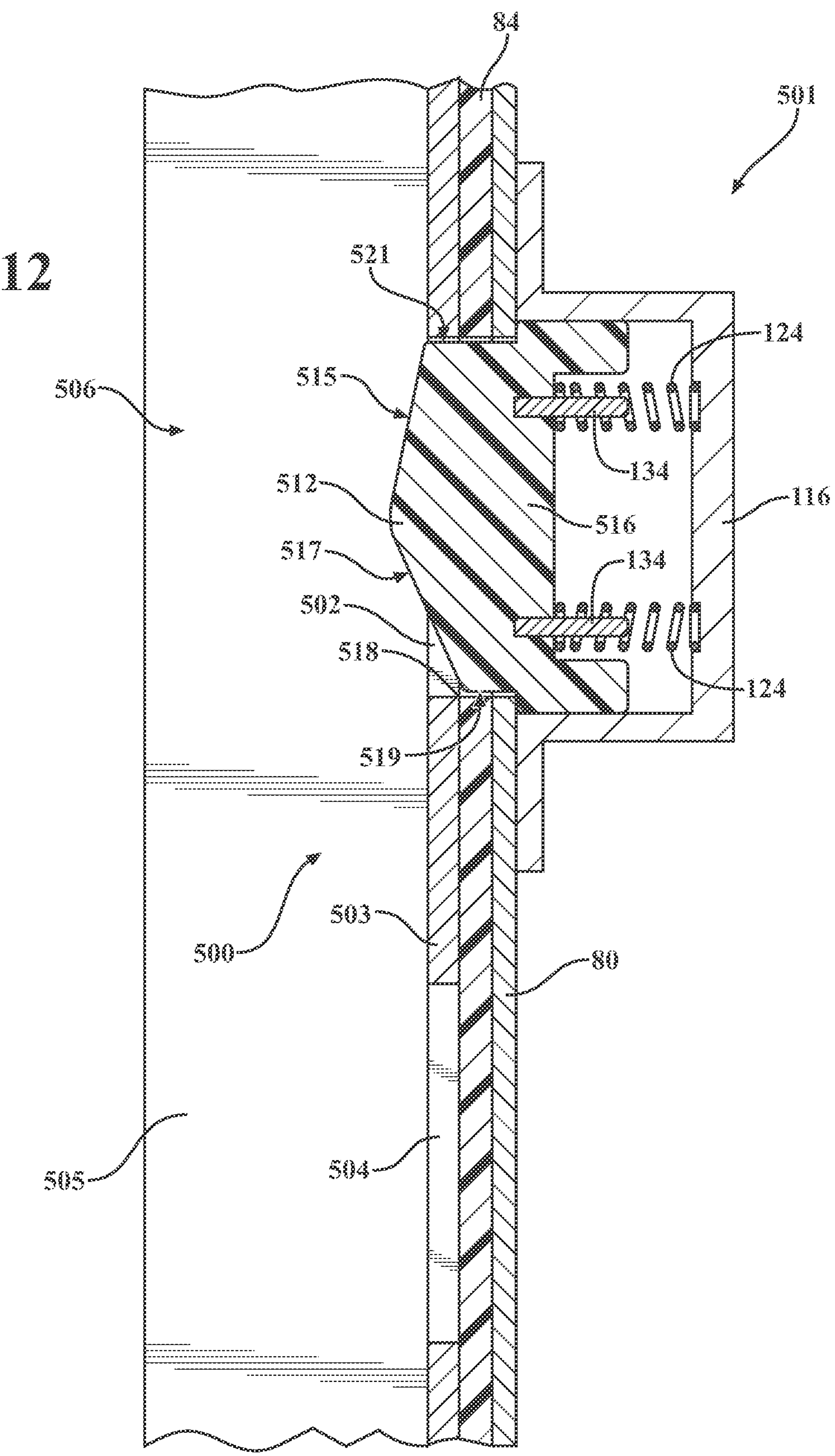
FIG. 12 is a cross-sectional view of an alternative telescoping support and an alternative locking device.

Referring to FIG. 12, an alternative telescoping support 500 with alternative locking device 501 is shown. The telescoping support 500 comprises longitudinally spaced first and second catches 502, 504 defined in an inner frame member 503. The locking device 501 comprises an alternative latch 506 configured to engage either of the first and second catches 502, 504 in a locked position to provide first and second extended positions. The inner frame member 503 comprises an inner channel 505 for receiving the slide member (not shown) to disengage the latch 506 from either of the first and second catches 502, 504 in the same manner as previously described.

A tip 512 of the latch 506 has a different profiled surface as compared to the prior embodiments. In this embodiment, an upper portion 515 of the profiled surface is the same as the embodiment of FIGS. 2-5, but a lower portion 517 differs in that the profiled surface extends further toward the housing 116. As a result of this configuration, a lower surface 519 of main body 516 no longer extends into the first and second catches 502, 504, when in the locked position (shown in FIG. 12). An upper surface 521 of the main body 516, however, still extends into the first and second catches 502, 504 in the locked position, as in the prior embodiments.

When the latch 506 is located in the first catch 502, the telescoping support 500 is unable to move downwardly due to the upper surface 521 of the main body 516 being present in the first catch 502. However, the telescoping support 500 can be further raised upwardly since an edge 518 of the inner frame member 503 defining the first catch 502 can engage the lower portion 517 of the profiled surface and disengage the latch 506 from the first catch 502 until the telescoping support 500 is raised to a level in which the second catch 504 is aligned with the latch 506. The latch 506 then automatically engages the second catch 504 to provide the second extended position.

In other embodiments, additional catches could be employed to provide further extended positions. For instance, additional catches could provide three or more extended positions. Additionally, one or more latches could be configured to engage the catches. So, in some embodiments, two or more catches and/or two or more latches can be employed. Smaller, more closely spaced catches could be employed to provide smaller increments of extension between extended positions while larger, further spaced catches could be employed to provide larger changes in extension between extended positions. Additionally, the latches can be configured to act as ratchets (such as FIG. 12) to allow continuous movement of the telescoping support in one direction into each of the several extended positions while not allowing movement in an opposite direction without releasing the latches.

Figure 13A:
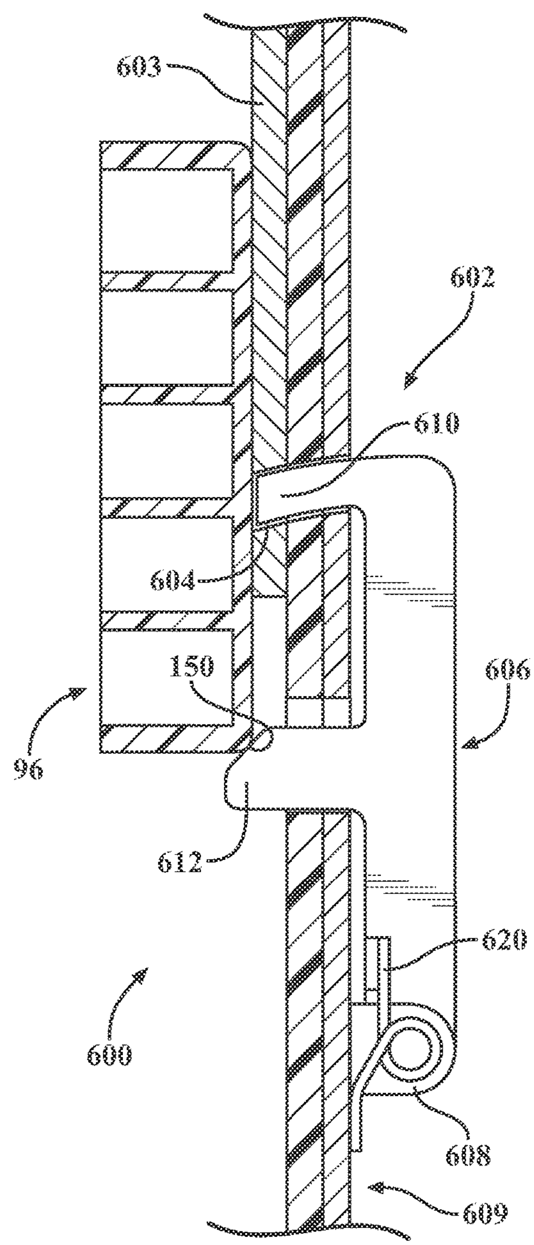
FIGS. 13A and 13B are cross-sectional views of another alternative locking device.
Figure 13B:
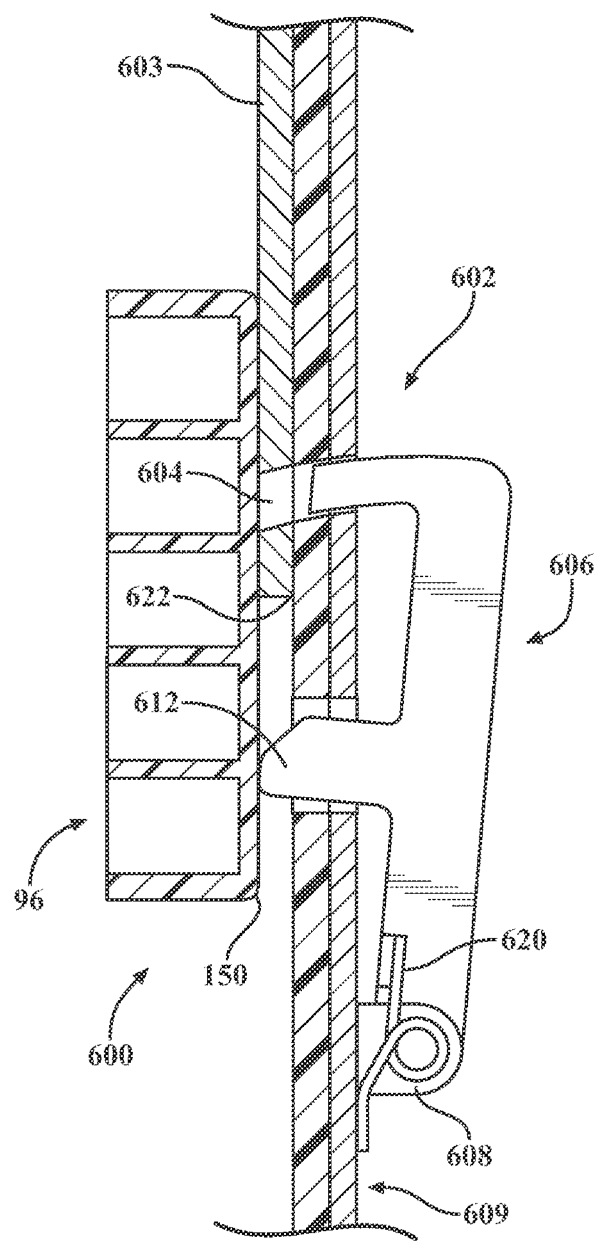

Referring to FIGS. 13A and 13B, another alternative telescoping support 600 and alternative locking device 602 are shown. In this embodiment, the telescoping support 600 comprises an inner frame member 603 comprising a catch 604. The locking device 602 comprises a latch 606 for engaging the catch 604 in the locked position. The latch 606 is pivotally connected to a bracket 608. The bracket 608 is fixed to a base support 609. The latch 606 has an engagement portion 610 for fitting into the catch 604 in the locked position. The latch 606 also has a release portion 612 for being engaged by the slide member 96 when the accessory (not shown) is being moved to the stowed position.

The release portion 612 is shaped so that the release portion 612 does not inadvertently engage the catch 604 when the telescoping support 600 is being raised to the extended position shown in FIG. 13A. To release the latch 606, the deactivator portion 150, e.g., the lower edge of the slide member 96, engages the release portion 612 and pivots the engagement portion 610 of the latch 606 away from the catch 604 against a biasing force of torsion spring 620. This causes the engagement portion 610 to withdraw from the catch 604 thereby releasing the telescoping support 600 and allowing the telescoping support 600 to be moved downwardly to the collapsed position. Upon further downward movement of the telescoping support 600, a lower edge 622 of the inner frame member 603 also engages the release portion 612 to further pivot the latch 606 out of engagement. Other shapes of the release portion 612 are contemplated. For instance, the release portion 612 may have a rounded or semi-spherical profile. The release portion 612 may be any shape capable of being engaged by the deactivator portion 150 of the slide member 96.

Figure 14:
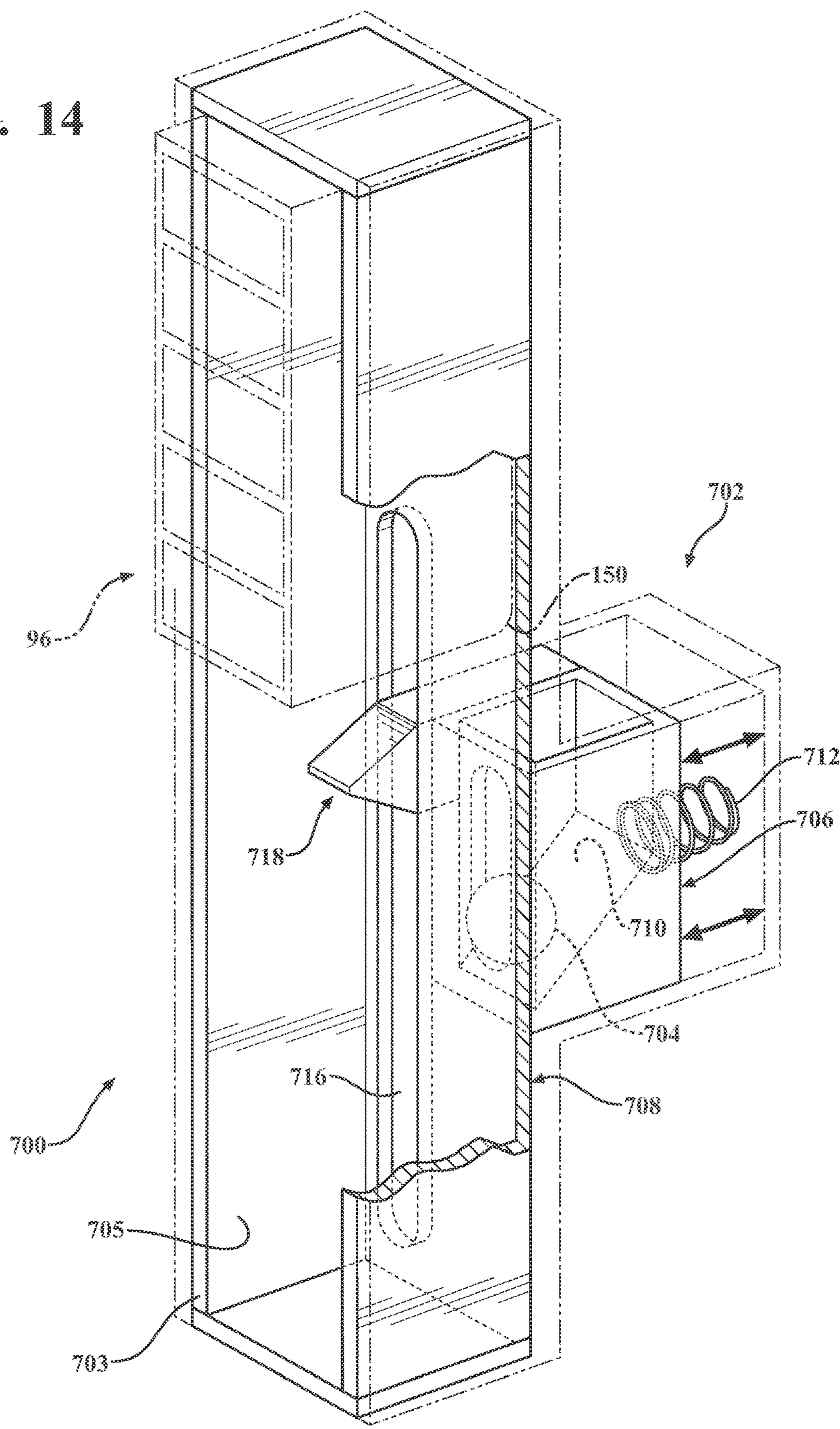
FIG. 14 is a perspective and partially cross-sectional view of another alternative locking device.
Figure 15A:
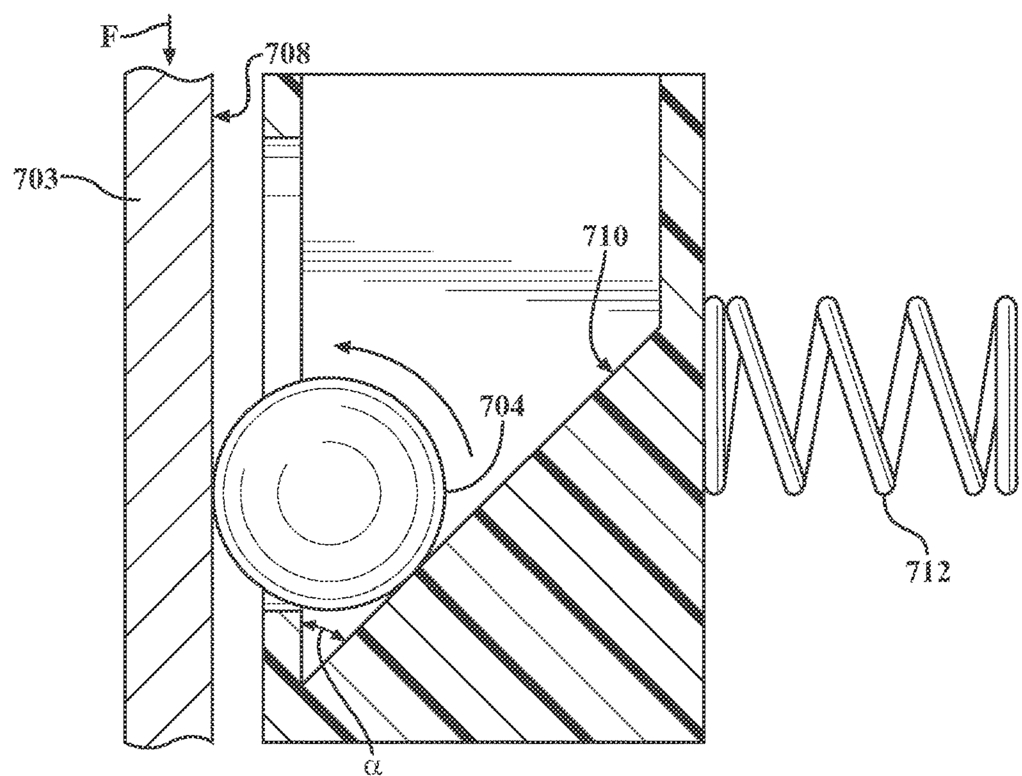
FIGS. 15A and 15B are cross-sectional views of the alternative locking device of FIG. 14.
Figure 15B:
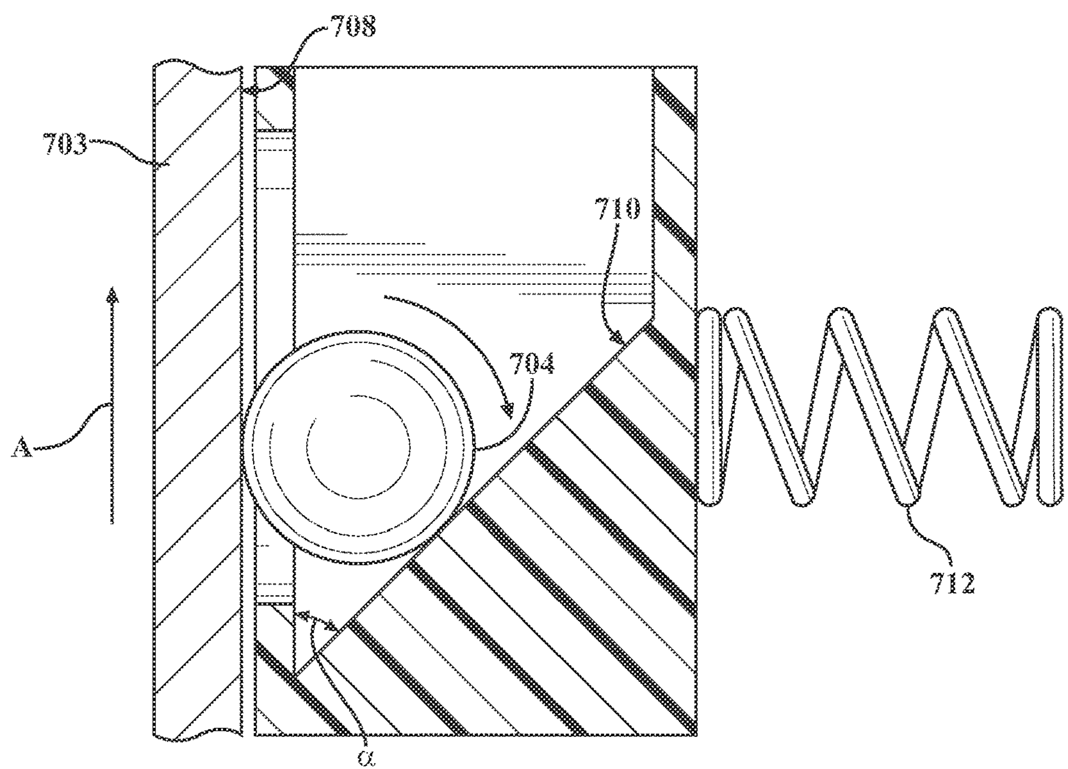

Referring to FIGS. 14, 15A, and 15B, another alternative telescoping support 700 and alternative locking device 702 are shown. The alternative telescoping support 700 comprises an inner frame member 703 comprising an inner channel 705. In this embodiment, the locking device 702 comprises a locking member 704 and a wedge member 706. The inner frame member 703 has an outer surface 708 and the wedge member 706 is operable to wedge the locking member 704 against the outer surface 708 to releasably engage the outer surface 708 and hold the telescoping support 700 in the extended position. The inner frame member 803 is arranged along a longitudinal axis and the wedge member 706 comprises a wedge surface 710 arranged at an acute angle $\alpha$ to the longitudinal axis.

The locking device 702 comprises a biasing device 712 applying a biasing force to the wedge member 706 to bias the wedge surface 710 toward the inner frame member 703. The biasing device 712 is shown as a compression spring in this embodiment. Other types of biasing devices 712 are also contemplated. As shown in FIG. 15A, the inner frame member 703 of the telescoping support 700 is generally immovable in a first direction when the locking member 704 is wedged against the outer surface 708 by the wedge surface 710. When a force F is applied to move the inner frame member 703 in the first direction, the locking member 704 is urged to roll in a manner (shown by arrow) that further wedges the locking member 704 by further compressing the biasing device 712.

As shown in FIG. 15B, the inner frame member 703 of the telescoping support 700 is movable in a second direction, opposite the first direction, to infinite extended positions, as shown by arrow A. When the inner frame member 703 is moved in the second direction, the locking member 704 is urged to roll up the wedge surface 710 and away from being wedged between the outer surface 708 and the wedge surface 710 (shown by arrow). Consequently, the biasing device 712 is relaxed. As a result, the inner frame member 703 of the telescoping support 700 is free to move in the second direction. The locking member 704 is a roller, such as a ball, in the embodiment shown.

Referring back to FIG. 14, the inner frame member 703 comprises a slot 716 for receiving a release member 718. The release member 718 is fixed to the wedge member 706 to move with the wedge member 706. The release member 718 is located in the slot 716 and rides in the slot 716 as the slot 716 moves when the telescoping support 700 moves from the collapsed position to the various extended positions. To disengage the wedge member 706 so that the telescoping support 700 can be moved back to the collapsed position, the deactivator portion 150 of slide member 96 engages a profiled surface of the release member 718 to drive the release member 718 laterally (shown by arrows) against the bias of the biasing device 712. This pulls the locking member 704 out of engagement with the outer surface 708 of the inner frame member 703 allowing the telescoping support 700 to freely move in the first direction to the collapsed position. Other shapes of the release member 718 are contemplated. The release member 718 may have only a single ramped surface or may have a rounded or semi-spherical profile. The release member 718 and the deactivator portion 150 may employ other shapes configured to interact so that the deactivator portion 150 is able to engage the release member 718 and disengage the wedge member 706.

Figure 16:
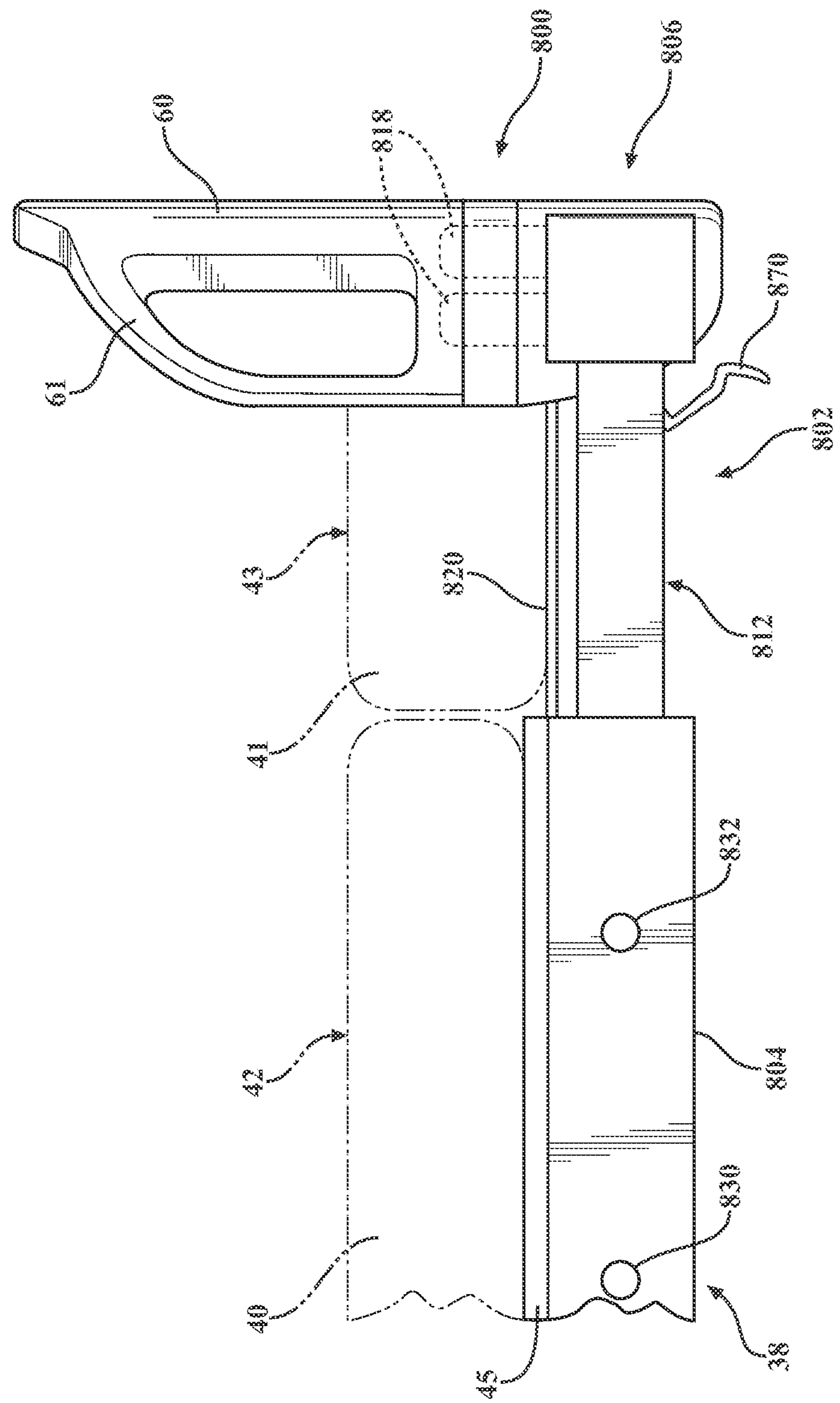
FIG. 16 is an elevational view of an extension in an extended position.
Figure 17:
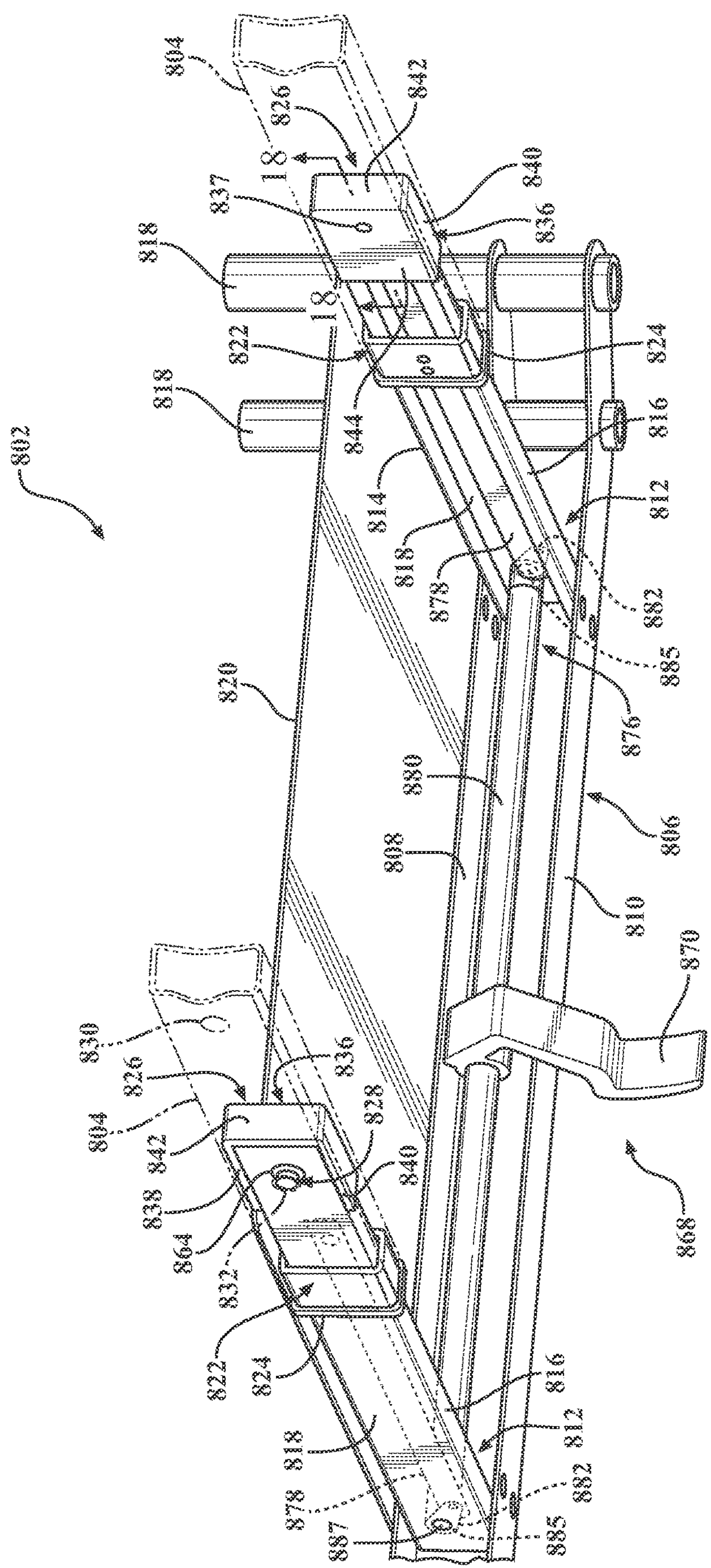
FIG. 17 is a perspective view of the extension.

Referring to FIGS. 16 and 17 an alternative telescoping assembly 800 is shown. This alternative telescoping assembly 800 comprises an extension 802 that is manually movable by a user relative to the intermediate frame 38 of the support structure 36 from a stowed position to an extended position. The extension 802 provides auxiliary support for the patient in the extended position. In the version shown in FIG. 16, the extension 802 is also referred to as a bed extension to extend a foot end of the patient support apparatus 30 to accommodate patients of greater than average height.

The mattress 40 provides the primary patient support surface 42 for supporting the patient. The primary patient support surface 42 extends longitudinally between head and foot ends. The footboard 60 is coupled to the extension 802 to move with the extension 802 from the stowed position to the extended position shown in FIG. 16. When the extension 802 is moved to the extended position, the footboard 60 moves away from the foot end of the primary patient support surface 42. This creates a gap between the foot end of the primary patient support surface 42 and the footboard 60. An auxiliary mattress 41 with an auxiliary patient support surface 43 is positioned in the gap to extend the patient support surface. In some embodiments, the extension 802 is movable at least twelve inches from the stowed position to the extended position. In other embodiments, the extension 802 is able to move less or more than twelve inches and may be extendable to multiple, discrete, extended positions.

The intermediate frame 38 comprises a pair of longitudinally oriented frame members 804 (see hidden lines in FIG. 17) to support the extension 802. The frame members 804 are spaced apart in a parallel relationship. Each of the frame members 804 have a hollow tubular shape with rectangular outer walls, e.g., rectangular tubing. In other embodiments, the frame members 804 may be cylindrical or other shapes or a single frame member may be employed. Various structures are contemplated to support the extension 802 during movement between the stowed position and the extended position.

The extension 802 comprises a base structure 806 with upper and lower base flanges 808, 810. Legs 812 are fixed to the base structure 806 between the base flanges 808, 810. The legs 812 may be fixed to the base flanges 808, 810 by welding, fasteners, or other suitable methods. The legs 812 extend from the base structure 806 into the frame members 804 to slide relative to the frame members 804. More specifically, the legs 812 are spaced apart in a parallel relationship and otherwise arranged so that the legs 812 slide inside the frame members 804. Each of the legs 812 comprises upper and lower leg flanges 814, 816 and a side wall 818 extending between the leg flanges 814, 816.

Posts 818 are fixed to the base flanges 808, 810 of the base structure 806. Only two posts 818 are shown at one end of the base structure 806, but two identical posts 818 (not shown) are also positioned at an opposite end of the base structure 806. The footboard 60 has corresponding sockets to receive the posts 818 (see FIG. 16). The footboard 60 is removably coupled to the base structure 806 via the sockets. In other embodiments, the footboard 60 is fixed to the base structure 806 and thereby integrated into the extension 802. In still other embodiments, the footboard 60 is absent.

Panel 820 is fixed to the upper base flange 808 of the base structure 806 by welding, fasteners, or other suitable methods. The panel 820 extends from the upper base flange 808 and over the legs 812 to provide a support surface upon which the auxiliary mattress 41 can be placed. As shown in FIG. 16, the panel 820 slides relative to a foot section 45 of the patient support deck 44 as the extension 802 moves between the stowed position and the extended position. The panel 820 may simply slide beneath the foot section 45 of the patient support deck 44 when the extension 802 is moved to the stowed position. In other embodiments, a cross member (not shown) is disposed between the frame members 804. The panel 820 slides on top of the cross member during movement between the stowed and extended positions.

A bearing sleeve 822 is disposed in ends of each of the frame members 804 to slidably receive the legs 812. The bearing sleeves 822 may be formed of PTFE or similar materials. This helps to facilitate smooth sliding of the legs 812 in the frame members 804. The bearing sleeves 822 are sized to fit snugly inside ends of the frame members 804. Each bearing sleeve has an end flange 824 sized to abut the ends of the frame members 804.

Locking devices 826 are operable to releasably hold the extension 802 relative to the frame members 804 in the stowed position and the extended position(s). The locking devices 826 comprise locking elements 828 that are arranged to releasably engage the frame members 804 to lock the legs 812 to the frame members 804 in predetermined longitudinal locations associated with the stowed position and the extended position(s).

In the embodiment shown, the locking elements 828 are latches in the form of shear pins. In other embodiments, the locking elements may comprise detents for temporary holding, snap-lock engagements, friction locks, magnetic locks and the like. The locking elements 828 are coupled to the legs 812 of the extension 802 to move with the extension 802 relative to the frame members 804 from the stowed position to the extended position. In other embodiments, the locking elements 828 may be coupled to the frame members 804 to remain longitudinally fixed as the extension 802 moves.

Each of the frame members 804 comprises openings 830, 832 in outer walls of the frame members 804 that are sized to receive the locking elements 828. The openings 830, 832 are placed at discrete, spaced locations. The openings 830, 832 comprise a first opening 830 associated with the stowed position and a second opening 832 associated with the extended position. In embodiments in which the locking elements 828 are coupled to the frame members to remain longitudinally fixed to the frame members, the openings are defined in the legs. In embodiments having multiple, extended positions, additional openings are present in the frame members 804 for the other extended positions.

Each of the locking devices 826 comprises a housing 836 connected to ends of the legs 812. The housings 836 support the locking elements 828 on the legs 812 so that the locking elements 828 move with the legs 812 when the extension 802 moves between the stowed position and the extended position. Fasteners 837 attach the housings 836 to each of the legs 812. The housings 836 may also be press fit on the legs 812, welded to the legs, or attached using other suitable methods.

Each housing 836 comprises a top wall 838, a bottom wall 840, and an end wall 842. A side wall 844 extends between the top wall 838 and bottom wall 840 on one side of the housing 836. The housings 836 are open on the opposite side to receive the legs 812. More specifically, the leg flanges 814, 816 of each of the legs 812 fit snugly within the respective housing 836 between the top wall 838 and the bottom wall 840. In other embodiments, the housings fit between the leg flanges 814, 816 such that the top and bottom walls are snugly disposed between the leg flanges 814, 816. The housings 836 are formed of a material suitable for smooth sliding in the frame members 804, such as PTFE. In embodiments in which the housings fit between the leg flanges 814, 816, a rotatable guide wheel (not shown) may be attached to the end of each leg 812 adjacent the housing to facilitate sliding of the legs 812 inside the frame members 804.

Referring to FIGS. 18A, 18B, and 19-21, each housing 836 comprises a guide 846 disposed on the side wall 844 and extending from the side wall 844. The guide 846 comprises a pocket 848 for receiving one of the locking elements 828. The guide 846 is shown in the form of two arcuate wall sections 850, 852 of a partial hollow cylinder, with gap 854 (see FIG. 19). The gap 854 is provided to accommodate the shape of the locking elements 828. In particular, referring to FIG. 21, each locking element 828 is T-shaped and comprises a body 860 and pegs 862 that are fixed to the body 860 and extend radially outwardly from the body 860. The gaps 854 are sized and shaped to receive the pegs 862. The body 860 of each locking element 828 extends from the pegs 862 and protrudes through an opening 864 in the side wall 818 of the leg 812 to engage one of the openings 830, 832 in the frame 804.

Figure 18A:
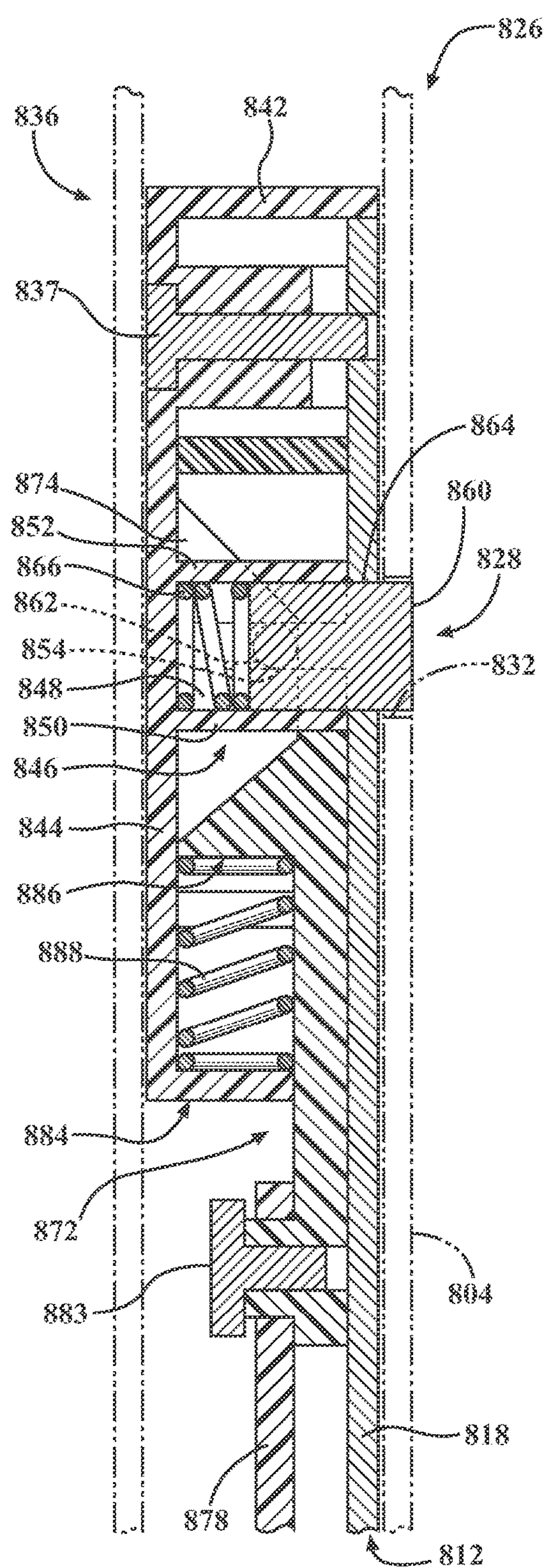
FIGS. 18A and 18B are cross-sectional views of a locking device in locked and unlocked positions.
Figure 18B:
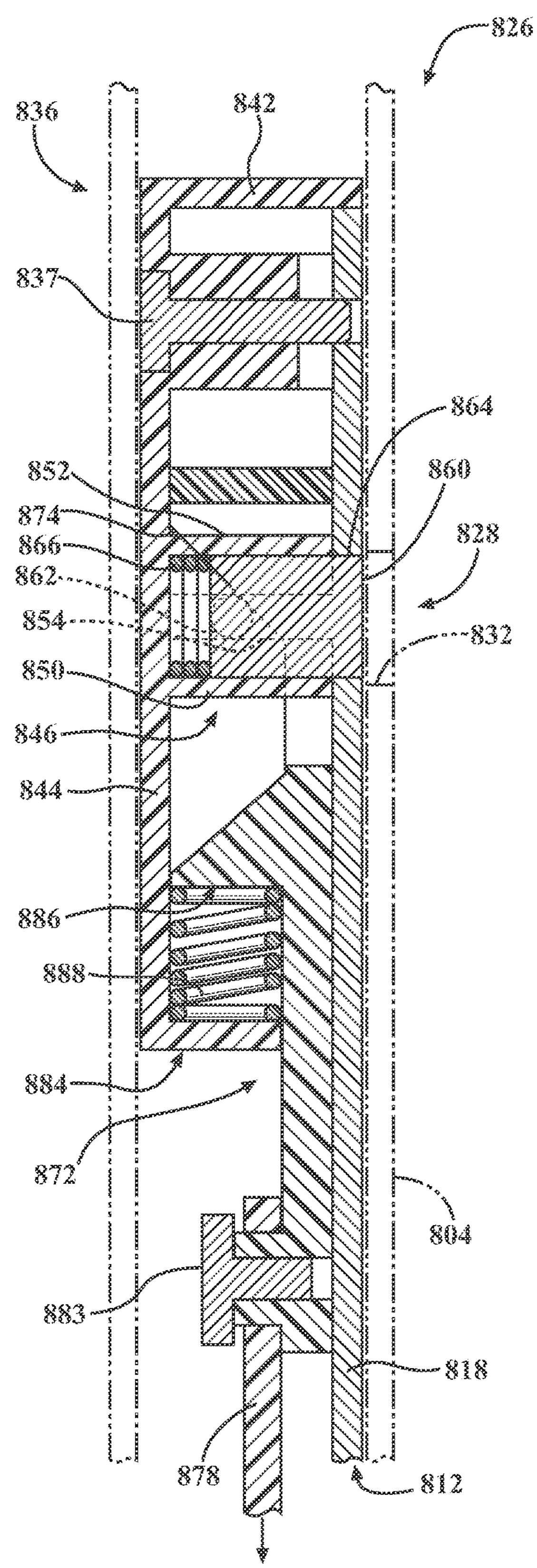
Figure 19:
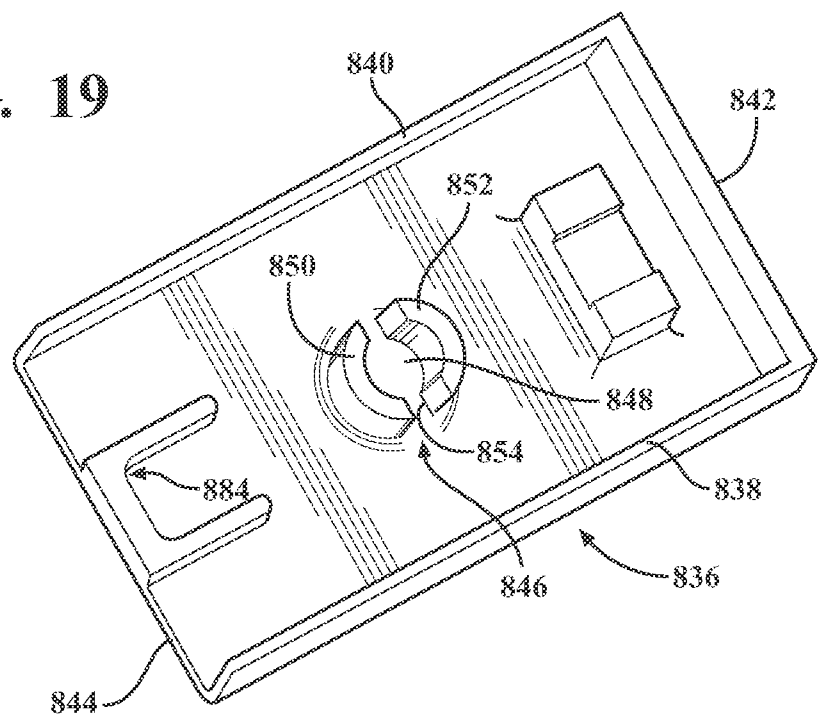
FIG. 19 is a perspective view inside of a housing of the locking device of FIGS. 18A and 18B.
Figure 20:
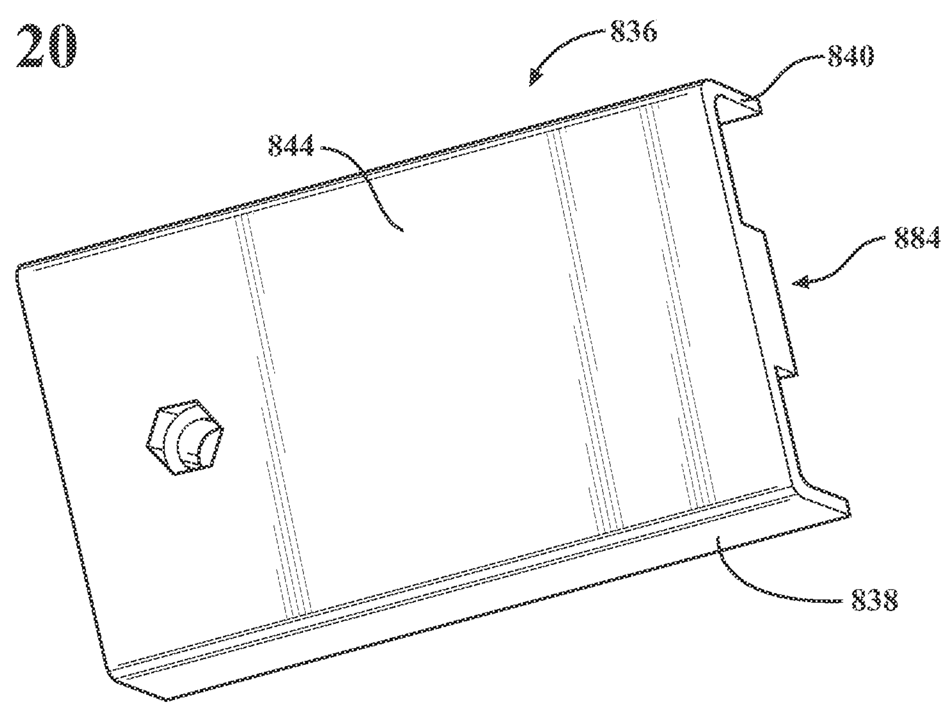
FIG. 20 is a perspective view outside of the housing of the locking device of FIGS. 18A and 18B.

A lock biasing device 866 is located in each of the housings 836. The lock biasing device 866 is located between the side wall 844 of the housing 836 and the locking element 828. The lock biasing devices 866 apply a biasing force to each of the locking elements 828 to normally bias the locking elements 828 into the locked position. In the embodiment shown, the lock biasing devices 866 normally bias the locking elements 828 toward engagement with one of the openings 830, 832 when one of the openings 830, 832 becomes aligned with the locking elements 828. The lock biasing device 866 shown in FIGS. 18A and 18B is a compression spring. Other biasing devices are also contemplated such as torsion springs, leaf springs, other resilient elements, and other devices suitable to normally place the locking elements 828 in the locked position.

Referring back to FIG. 17, a release mechanism 868 is operable to manipulate the locking elements 828 of the locking devices 826 to disengage the locking elements 828 from the frame members 804 and release the extension 802 for movement. The release mechanism 868 comprises a release handle 870 located and sized for grasping by the user so that the user can manipulate the release mechanism 868 to release the extension 802 for movement. In the embodiment shown, the release handle 870 extends downwardly, away from the extension 802, for easy access by the user beneath the extension 802. Other locations and configurations of the release handle 870 are also contemplated. For instance, the release handle 870 may be located outside a footprint of the patient support apparatus 30. The release handle 870 could also be located adjacent one of the foot end side rails 52, 56.

In the embodiment shown, the release handle 870 is integrated into the extension 802 such that the release handle 870 moves with the extension 802. More specifically, for instance, the release handle 870 is carried longitudinally with the extension 802, away from the foot end of the mattress 40, when the extension 802 is moved from the stowed position to the extended position, shown in FIG. 16.

Referring to FIGS. 18A, 18B, 22, and 23, the release mechanism 868 also comprises a pair of release members 872. The release members 872 are coupled to the release handle 870. The release members 872 slide relative to the locking elements 828 and longitudinally with respect to the patient support apparatus 30 upon one-handed actuation of the release handle 870 by the user. This movement of the release members 872 simultaneously urges the locking elements 828 away from the frame members 804 to disengage the locking elements 828 from the frame members 804 and release the extension 802 for movement.

Each of the release members 872 comprises a pair of ramps 874 that comprise a release surface. The release surface is configured to move the locking elements 828 and disengage the locking elements 828 from the frame members 804 upon actuation of the release handle 870 by the user. FIG. 18A shows one of the release members 872 prior to actuation. FIG. 18B shows the release member 872 after actuation. As shown in FIG. 18B, when the release member 872 is actuated, the ramps 874 operate to slide the pegs 862 in the gap 854 against the lock biasing device 866 thereby compressing the lock biasing device 866 and withdrawing the body 860 of the locking element 828 out of the opening 832.

Referring to FIGS. 17 and 18A, in the embodiment shown, linkage 876 couples the release members 872 to the release handle 870. The linkage 876 comprises a pair of links 878 and a cross member 880 with arms 882. The links 878 are pivotally coupled at one end to the release members 872 by pivot pins 883. The links 878 are pivotally coupled at an opposite end to the arms 882 by pivot pins 885. The cross member 880 has opposing ends rotatably coupled to the legs 812 of the extension 802 by pivot pins 887. The arms 882 are spaced apart and fixed to the cross member 880 to rotate with the cross member 880.

The release handle 870 is fixed to the cross member 880 at a location approximately equidistant between the opposing ends of the cross member 880. When the user grasps and rotates the release handle 870, the cross member 880 and arms 882 are likewise rotated, which pulls on both of the links 878 and slides both of the release members 872 relative to the locking elements 828 to simultaneously unlock the locking elements 828 in the manner previously described. Although the release handle 870 is described as being rotated by the user to release the extension 802, other forms of release actuator other than the rotating release handle 870 are contemplated. For instance, the release actuator may comprise a slider that moves linearly relative to the extension 802 to release the extension 802.

Various configurations of the linkage 876 are also contemplated to translate movement of the release handle 870 to the locking elements 828 so that one-handed operation of the release handle 870 unlocks the locking elements 828 from the frame members 80. For instance, the links 878 shown are elongate bars, but could comprise cables, chains, or other types of links. Additionally, the release handle 870 is shown fixed to the cross member 880, but could also be fixed to one of the links 878.

Each housing 836 comprises a first abutment structure 884 having three walls to define a first space. Likewise, each release member 872 comprises a second abutment structure 886 having three walls to define a second space. The first and second abutment structures 884, 886 cooperate in the manner shown in FIGS. 18A and 18B to define a pocket for receiving a release biasing device 888. The release biasing device 888 is shown in the form of a compression spring, but may take other forms previously mentioned. The release biasing device 888 is shown compressed in FIG. 18B as a result of actuation of the release handle 870. Owing to the biasing force applied by the release biasing device 888, when the user releases the release handle 870, the release biasing device 888 pushes the release member 872 back to a pre-actuation position, as shown in FIG. 18A, which also restores the release handle 870 to its pre-actuation position.

Figure 24:
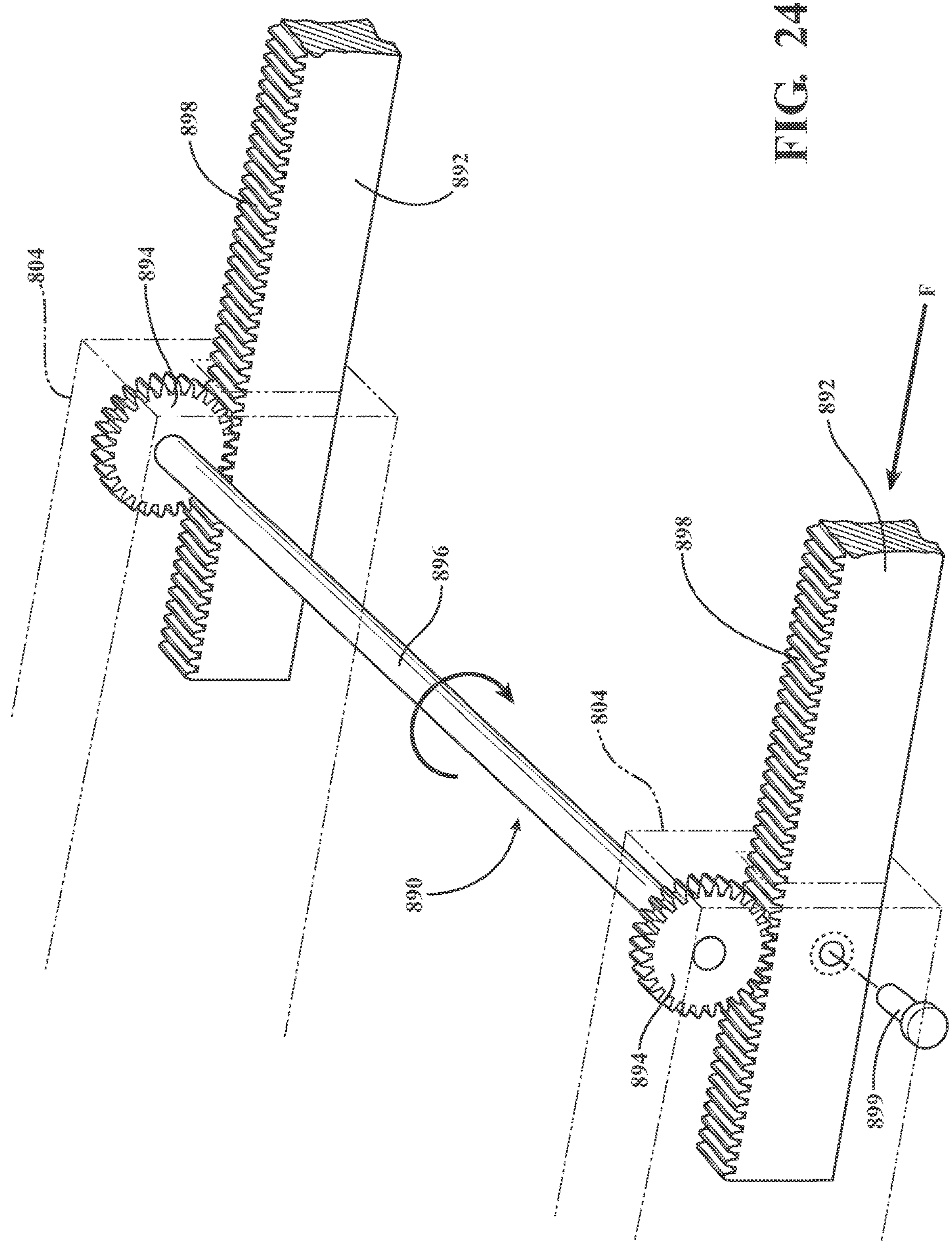
FIG. 24 is an illustration of a gear assembly for use with an extension.

Referring to FIG. 24, in some embodiments, a gear assembly 890 could be provided to time movement of legs 892 into the frame members 804 such that the legs 892 move in unison. The gear assembly 890 comprises timing gears 894 that are fixed together to rotate in unison by a cross bar 896. The cross bar 896 is rotatably coupled to the frame members 804. The cross bar 896 is arranged such that the cross bar 896 is allowed to rotate, but is fixed from other movement relative to the frame members 804. The timing gears 894 are located inside the frame members 804 as shown. The timing gears 894 engage teeth 898 on the legs 892. This engagement is maintained throughout the motion of the legs 892 between the stowed position and the extended position. As a result, if the user applies a greater force to one leg 892, as shown by force F, versus the other leg 892, the gear assembly 890 translates the force F to the other leg 892 so that the legs 892 move in unison. In these embodiments, a single locking element 899 may be used to lock both of the legs 892 to the frame members 804 since movement of the legs 892 is synchronized by the gear assembly 890.

Referring to FIGS. 25, 26A, 26B, and 27, a cable support 900 is provided for supporting a cable 902. The cable 902 may be any type of cable. The cable 902 may be a power cable, data cable, communication cable, and the like. In the embodiment shown, the cable 902 is disposed between the intermediate frame 38 and the footboard 60. The cable 902 is supported by the cable support 900, for example, during transition of the extension 802 from the stowed position to the extended position, and vice versa. The cable support 900 manages slack that would otherwise occur in the cable 902 without the cable support 900, for example, when the extension 802 is moved from the extended position to the stowed position and the cable 902 unduly hangs down beneath the extension 802, as illustrated by hidden lines in FIG. 26B. The cable support 900 prevents this condition.

The cable 902 has first and second connectors 904, 906 on opposing ends. The first connector 904 is connected to a first socket 908 on the intermediate frame 38. The second connector 906 is connected to a second socket 910 on the footboard 60. The cable 902 may be used to transmit power and/or data between a controller 912 mounted to the intermediate frame 38 and a user interface 914 integrated into the footboard 60, such as when the footboard 60 has on-board electronic controls.

The cable support 900 has a first end portion 916 connected to the intermediate frame 38 of the support structure 36 and a second end portion 918 connected to the base structure 806 of the extension 802. Each of the end portions 916, 918 comprise openings for receiving fasteners 925 to fix the end portions 916, 918 as indicated. The cable support 900 comprises a strip 920 of flexible material between the end portions 916, 918. The strip 920 comprises openings 922 for weaving the cable 902 therethrough to support the cable 902 as the extension 802 moves from the stowed position to the extended position. Eight openings 922 are shown, but more or fewer are possible in other embodiments. In some versions, at least two openings are present to enable weaving of the cable though the openings.

Figures 25, 26A:
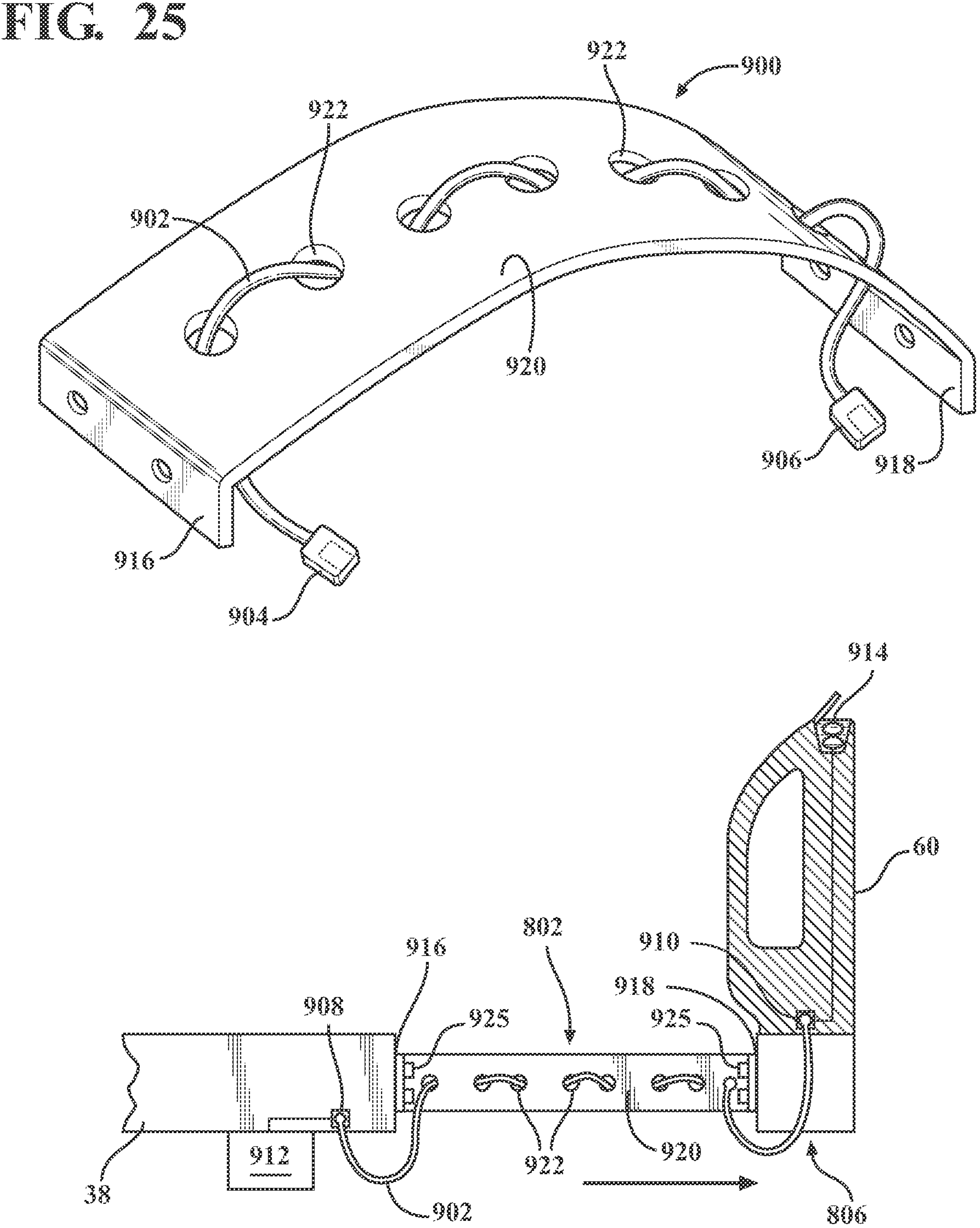

In the embodiment shown, the strip 920 of flexible material is arranged to flex such that the strip 920 limits motion of the cable 902. In one embodiment, the strip 920 limits motion to two degrees of freedom as the extension 802 moves from the stowed position to the extended position. In particular, in this embodiment, motion is limited to horizontal motion in a single x-y plane. The cable 902 is unable to move vertically and is also unable to pitch, yaw, or roll. This is best illustrated in FIGS. 26A and 26B. FIG. 26A shows the strip 920 in an expanded, unflexed state with the extension 802 in the extended position. FIG. 26B shows the strip 920 in a collapsed, flexed state, with the extension 802 moving toward the stowed position. To reach this state, the strip 920 has essentially been flexed in equal halves as shown in FIG. 27. By limiting motion of the cable 902, the cable 902 is unable to hang down in the manner shown in hidden lines in FIG. 26B.

It should be appreciated that the terms "include," "includes," and "including" have the same meaning as the terms "comprise," "comprises," and "comprising."

Several embodiments have been discussed in the foregoing description. However, the embodiments discussed herein are not intended to be exhaustive. The terminology which has been used is intended to be in the nature of words of description rather than of limitation. Many modifications and variations are possible in light of the above teachings.

What is claimed is:

1. A patient support apparatus comprising:

a base arranged for movement along floor surfaces;

an intermediate frame spaced above the base;

a patient support deck coupled to the intermediate frame and comprising a primary support surface for a patient;

an extension manually movable by a user relative to the intermediate frame from a stowed position to an extended position so that the extension provides auxiliary support for the patient in the extended position; and a cable support having a first end connected to the intermediate frame, a second end connected to the extension, and a strip of flexible material extending between the first end and the second end and defining a cable retainer for retaining a cable between the first end and the second end to support the cable as the extension moves from the stowed position to the extended position.

2. The patient support apparatus of claim 1, wherein the strip of flexible material of the cable support is arranged to flex such that the strip limits motion of the cable to two degrees of freedom as the extension moves from the stowed position to the extended position.

3. The patient support apparatus of claim 1, wherein the strip of flexible material of the cable support has a generally rectangular profile extending between the first end and the second end.

4. The patient support apparatus of claim 3, wherein the generally rectangular profile of the strip of flexible material defines:

a length defined in a longitudinal direction between the first end and the second end, and a height defined in a vertical direction relative to floor surfaces; and wherein the length is at least three times larger than the height.

5. The patient support apparatus of claim 3, wherein the generally rectangular profile of the strip of flexible material defines:

a length defined in a longitudinal direction between the first end and the second end, a height defined in a vertical direction relative to floor surfaces, and a thickness defined in a lateral direction perpendicular to the longitudinal direction and perpendicular to the vertical direction; and wherein the height is larger than the thickness.

6. The patient support apparatus of claim 5, wherein the length is larger than the height.

7. The patient support apparatus of claim 1, wherein the cable retainer of the cable support includes a plurality of openings for weaving the cable therethrough to support the cable.

8. The patient support apparatus of claim 1, further comprising:

a locking device operable to releasably hold the extension relative to the intermediate frame in the stowed position and the extended position; and a release mechanism operable to manipulate the locking device to release the extension for movement relative to the intermediate frame, the release mechanism being movable with the extension from the stowed position to the extended position.

9. The patient support apparatus of claim 8, wherein the primary support surface has a head end and a foot end and the primary support surface extends longitudinally between the head end and the foot end; and wherein the release mechanism includes a release handle longitudinally carried by the extension away from the foot end as the extension moves from the stowed position to the extended position.

10. The patient support apparatus of claim 9, further comprising a second locking device, the locking devices being spaced apart and cooperable to releasably hold the extension relative to the intermediate frame in the stowed position and the extended position; and wherein each of the locking devices comprises a locking element and the release mechanism is configured to manipulate the locking elements simultaneously to release the extension for movement relative to the intermediate frame.

11. The patient support apparatus of claim 10, wherein the release mechanism is configured to manipulate the locking elements simultaneously to release the extension for movement relative to the intermediate frame upon one-handed operation of the release handle by the user.

12. The patient support apparatus of claim 10, wherein each of the locking devices further comprises a biasing device, the biasing devices being arranged to bias the locking elements into engagement with one of the intermediate frame or the extension; and wherein the release mechanism further comprises a pair of release members movable to disengage the locking elements from the intermediate frame to release the extension for movement relative to the intermediate frame.

13. The patient support apparatus of claim 12, wherein the release mechanism further comprises a release actuator and a pair of links coupled to the release members, the release actuator being manipulable by the user to simultaneously move the links and the release members to disengage the locking elements from the intermediate frame.

14. The patient support apparatus of claim 13, wherein the release actuator comprises a cross member having opposing ends rotatably coupled to the extension, a pair of arms fixed to the cross member and coupled to the links and the release handle; and wherein the release handle is manually operable to rotate the cross member and the arms to move the links and the release members to disengage the locking elements from the intermediate frame.

15. The patient support apparatus of claim 8, wherein the locking device is operable to engage one of the intermediate frame or the extension at a first discrete location when the extension is in the stowed position and at a second discrete location, longitudinally spaced from the first discrete location, when the extension is in the extended position.

16. The patient support apparatus of claim 1, further comprising a footboard mounted to the extension to move with the extension from the stowed position to the extended position.

* * * * *